(12) United States Patent
Roche et al.

(10) Patent No.: US 7,582,656 B2
(45) Date of Patent: Sep. 1, 2009

(54) GUANIDINE DERIVATIVES AND THERAPEUTIC USES THEREOF

(75) Inventors: Didier Roche, Saclay (FR); Bruno Roux, Lyons (FR); Isabelle Berard, Villard les Dombes (FR)

(73) Assignee: Merck Patent Gesellschaft, Darmstadt (DE)

( * ) Notice: Subject to any disclaimer, the term of this patent is extended or adjusted under 35 U.S.C. 154(b) by 28 days.

(21) Appl. No.: 11/572,663

(22) PCT Filed: Jun. 28, 2005

(86) PCT No.: PCT/EP2005/006929

§ 371 (c)(1),
(2), (4) Date: Jan. 25, 2007

(87) PCT Pub. No.: WO2006/010422

PCT Pub. Date: Feb. 2, 2006

(65) Prior Publication Data

US 2008/0004315 A1    Jan. 3, 2008

(30) Foreign Application Priority Data

Jul. 26, 2004  (FR) .................................. 04 08237

(51) Int. Cl.
*A61K 31/445* (2006.01)
*A61K 31/40* (2006.01)
*A61K 31/155* (2006.01)
*C07D 211/26* (2006.01)
*C07D 207/06* (2006.01)
*C07D 279/18* (2006.01)

(52) U.S. Cl. ...................... 514/331; 514/408; 514/634; 546/231; 548/566; 564/238

(58) Field of Classification Search ................ 514/329, 514/426, 331, 408, 634; 426/634; 546/224, 546/231; 548/557, 566; 564/237, 238
See application file for complete search history.

(56) References Cited

U.S. PATENT DOCUMENTS

| 5,925,645 A | 7/1999 | Schmidt et al. |
| 2004/0224875 A1* | 11/2004 | Schilling et al. ............... 514/2 |
| 2006/0069100 A1 | 3/2006 | Giannessi et al. |

FOREIGN PATENT DOCUMENTS

| EP | 0 796 846 A | 9/1997 |
| WO | WO 2004/054967 A | 7/2004 |

OTHER PUBLICATIONS

Database CA, Chemical Abstracts Service, Columbus Ohio, US, Ovsepyan, T.R. et al., Synthesis of Substituted Guanidines, 1996, pp. 696-703.

* cited by examiner

*Primary Examiner*—Kamal A Saeed
*Assistant Examiner*—Kristin Bianchi
(74) *Attorney, Agent, or Firm*—Millen, White, Zelano & Branigan, P.C.

(57) ABSTRACT

Compounds of the formula (I):

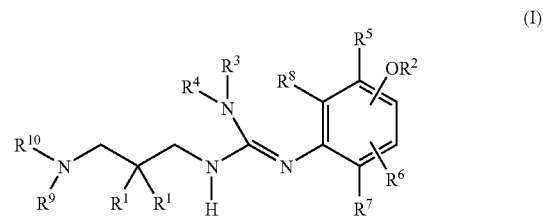

Figure 1:
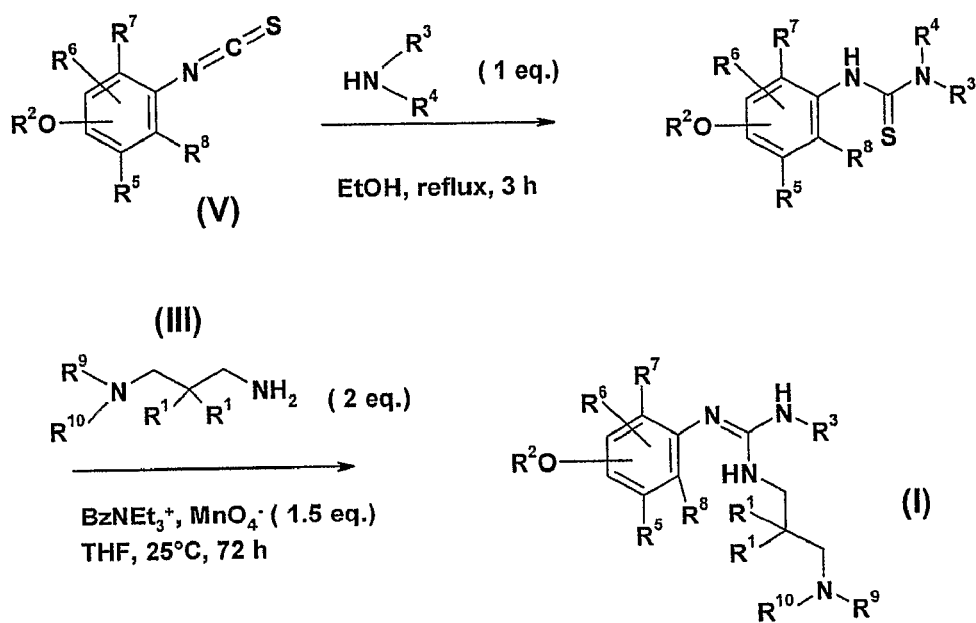

in which the radicals R and $R^1$ to $R^{10}$ are as defined in the description,
processes for the preparation of them,
use thereof for the treatment of cardiovascular diseases, and pharmaceutical compositions comprising them.

26 Claims, 3 Drawing Sheets

Scheme 1 :

Scheme 2:

Scheme 3:

GUANIDINE DERIVATIVES AND THERAPEUTIC USES THEREOF

The present invention relates to guanidine derivatives, to processes for the preparation of these derivatives, to pharmaceutical compositions comprising these derivatives, and to the use of these derivatives as CETP repressors, for the prevention and treatment of cardiovascular diseases, and in particular atherosclerosis and type II diabetes.

Atherosclerosis, and cardiovascular diseases in general, are one of the main causes of death in developed countries. Despite the efforts directed towards minimising the risk factors, such as smoking, a sedentary lifestyle and an unbalanced diet, and also the therapeutic treatments for dyslipidaemia using pharmaceutical compositions, death due to myocardial infarction and other cardiovascular diseases remains very high.

It has been demonstrated that the risks of cardiovascular diseases are highly dependent on the levels of low-density lipoproteins (LDL) in the blood plasma.

Whereas high levels of triglycerides and of LDL cholesterol contribute positively to the risks of developing cardiovascular diseases, high levels of high-density lipoprotein (HDL) cholesterol reduce the risks of developing these diseases. Thus, dyslipidaemia does not have only one risk profile for cardiovascular diseases, but may include one or more lipid dysfunctions.

Among the many factors acting on the levels of triglycerides, LDL and HDL, CETP (cholesteryl ester transfer protein) plays an important role. CETP catalyses the transfer and exchange of triglycerides and of cholesterol esters between the HDLs of the plasma and the low-density lipoproteins (LDL) and very-low-density lipoproteins (VLDL) which contain triglycerides. If the action of CETP on the levels of these various lipids contained in the lipoproteins is increased, it is thus considered as being pro-atherogenic, in particular in the case of individuals in whom the lipid profile represents a high risk of cardiovascular diseases.

Thus, modulating the activity of CETP, either by direct inhibition or by controlled regulation of CETP expression, may be considered as a possible means of therapeutic treatment (see, for example, Kushwaha et al., *J. Lipid Research*, 34, (1993), 1285-1297).

Accordingly, a considerable amount of research has been directed towards CETP inhibitors, and has given rise to inhibitors of peptide and non-peptide type. Among the latter, mention may be made of CETP inhibitors of tetrahydroquinoline type (described in patent application EP-A-0 818 448) or those of 2-arylpyridine type (EP-A-0 796 846), or alternatively those described in patent application EP-A-0 818 197, to mention but a few.

Despite the existence in the literature of all these inhibitors, there is nevertheless still a need for novel CETP inhibitors that are more effective, that have a longer duration of action, are more specific, show better absorption and better solubility and have fewer risks of side effects.

The present invention proposes to achieve these objectives, in total or in part, by means of novel compounds of guanidine structure.

More specifically, the invention relates to guanidine derivatives of the formula (I):

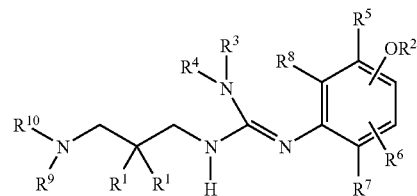

in which:
$R^1$ is chosen from a hydrogen atom and a $(C_1-C_6)$alkyl radical, or alternatively
the two radicals $R^1$ form, together with the carbon atom that bears them, a $(C_3-C_{10})$cycloalkyl radical;
$R^2$ is chosen from a $(C_1-C_{10})$alkyl radical, a $(C_2-C_{10})$alkenyl radical, a $(C_6-C_{18})$aryl$(C_1-C_{10})$alkyl radical, a $(C_1-C_6)$alkyl-O—$(C_1-C_{10})$alkyl radical and a $(C_3-C_{10})$cycloalkyl$(C_1-C_{10})$alkyl radical;
$R^3$ and $R^4$, which may be identical or different, are chosen independently from a hydrogen atom, a $(C_1-C_{10})$alkyl radical, a $(C_2-C_{10})$alkenyl radical, a $(C_6-C_{18})$aryl$(C_1-C_{10})$alkyl radical, a $(C_1-C_6)$alkyl-O—$(C_1-C_{10})$alkyl radical and a $(C_3-C_{10})$cycloalkyl$(C_1-C_{10})$alkyl radical, or alternatively
$R^3$ and $R^4$ form, together with the nitrogen atom that bears them, a 3- to 9-membered heterocycle;
$R^5$, $R^6$, $R^7$ and $R^8$, which may be identical or different, are chosen independently from a hydrogen atom, a $(C_1-C_{10})$ alkyl radical, a $(C_1-C_{10})$-alkenyl radical and a $(C_1-C_6)$ alkyl-O— radical; and
$R^9$ and $R^{10}$, which may be identical or different, are chosen independently from a hydrogen atom and a $(C_1-C_6)$alkyl radical, or alternatively
$R^9$ and $R^{10}$ form, together with the nitrogen atom that bears them, a 3- to 7-membered heterocycle;
the optical and geometrical isomers, oxide forms and tautomeric forms thereof, and also the pharmaceutically acceptable addition salts thereof with acids or bases.

The acids that can be used for the formation of salts of compounds of the formula (I) are mineral or organic acids. The resulting salts are, for example, the hydrochlorides, hydrobromides, sulfates, hydrogen sulfates, dihydrogen phosphates, citrates, maleates, fumarates, trifluoroacetates, 2-naphthalenesulfonate and para-toluenesulfonate.

The bases that can be used for the formation of salts of compounds of the formula (I) are organic or mineral bases. The resulting salts are, for example, the salts formed with metals and especially alkali metals, alkaline-earth metals and transition metals (such as sodium, potassium, calcium, magnesium or aluminium) or with bases, for instance ammonia, or secondary or tertiary amines (such as diethylamine, triethylamine, piperidine, piperazine or morpholine) or with basic amino acids, or with osamines (such as meglumine) or with amino alcohols (such as 3-aminobutanol and 2-aminoethanol).

The invention especially covers the pharmaceutically acceptable salts, but also salts allowing a suitable separation or crystallisation of the compounds of the formula (I), such as the salts obtained with chiral amines or with chiral acids.

Examples of chiral amines that can be used include quinine, brucine, (S)-1-(benzyloxymethyl)propylamine (III), (−)-ephedrine, (4S,5R)(+)-1,2,2,3,4-tetramethyl-5-phenyl-1,3-oxazolidine, (R)-1-phenyl-2-p-tolylethylamine, (S)-phenylglycinol, (−)-N-methylephedrine, (+)(2S,3R)-4-dimethylamino-3-methyl-1,2-diphenyl-2-butanol, (S)-phenylglycinol and (S)-α-methylbenzylamine, or a mixture of two or more thereof.

Examples of chiral acids that can be used include (−)-D-di-O-benzoyltartaric acid, (−)-L-di-O-benzoyltartaric acid, (−)-di-O,O'-p-toluyl-L-tartaric acid, (+)-di-O,O'-p-toluyl-D-tartaric acid, (R)(+)-malic acid, (S)(−)-malic acid, (+)-camphanic acid, (−)-camphanic acid, R(−)-1,1'-binaphthalene-2,2'-diyl hydrogen phosphate acid, (S)(+)-1,1'-binaphthalene-2,2'-diyl hydrogen phosphate acid, (+)-camphoric acid, (−)-camphoric acid, (S)(+)-2-phenylpropionic acid, (R)(−)-2-phenylpropionic acid, D-(−)-mandelic acid, L-(+)-mandelic acid, D-tartaric acid and L-tartaric acid, or a mixture of two or more thereof.

The chiral acid is preferably chosen from (−)-di-O,O'-p-toluyl-L-tartaric acid, (+)-di-O,O'-p-toluyl-D-tartaric acid, (R)(−)-1,1'-binaphthalene-2,2'-diyl hydrogen phosphate acid, (S)(+)-1,1'-binaphthalene-2,2'-diyl hydrogen phosphate acid, D-tartaric acid and L-tartaric acid, or a mixture of two or more thereof.

The invention also covers the optical isomers, in particular stereoisomers and diastereoisomers, where appropriate, of the compounds of the formula (I), and also mixtures of optical isomers in any proportion, including racemic mixtures.

The geometrical isomers, commonly referred to as cis and trans, or alternatively E and Z, are also included in the field of the present invention, in pure forms, or as mixtures in any proportion.

Depending on the nature of the substituents, the compounds of the formula (I) may also be in various tautomeric forms that are also included in the present invention, alone or as mixtures of two or more of them, in any proportion.

By way of example, if $R^3$ represents hydrogen, the compound of the formula (I) may be in the tautomeric form $(I_T)$ below:

octyl, methylheptyl, dimethylhexyl, nonyl, decyl, methylnonyl, dimethyloctyl and dodecyl.

The term "$(C_1-C_6)$alkyl radical" means a linear or branched hydrocarbon-based chain containing from 1 to 6 carbon atoms, optionally substituted by one or more groups defined below.

Examples of $(C_1-C_6)$alkyl radicals are methyl, ethyl, propyl, isopropyl, butyl, isobutyl, tert-butyl, pentyl, isopentyl, neopentyl, methylbutyl, ethyl-propyl, hexyl, isohexyl, neohexyl, methylpentyl, dimethylbutyl, ethylbutyl, and methylethylpropyl.

The term "$(C_1-C_6)$alkoxy radical" should be understood as being a $(C_1-C_6)$alkyl radical linked to a divalent oxygen atom.

The term "$(C_3-C_{10})$cycloalkyl radical" denotes a mono-, bi- or poly-cyclic hydrocarbon-based radical containing from 3 to 10 carbon atoms. Examples of $C_3-C_{10}$ cycloalkyl radicals are especially cyclopropyl, cyclobutyl, cyclopentyl, cyclohexyl, cycloheptyl, cyclooctyl and cyclodecyl radicals.

The term "$(C_2-C_{10})$alkenyl radical" means an aliphatic hydrocarbon-based group containing one or more unsaturations of vinyl type. Examples of alkenyl radicals are vinyl, prop-2-enyl, but-2-enyl, but-3-enyl, pent-2-enyl, pent-3-enyl, pent-4-enyl, 3-methylbut-2-enyl, hex-5-enyl, 4-ethylhex-3-enyl and the like.

Still within the context of the present invention, the term "$(C_6-C_{18})$aryl radical" means a mono-, bi-or polycyclic carbocyclic aromatic radical containing from 6 to 18 carbon atoms. Aryl radicals that may be mentioned include phenyl, naphthyl, anthryl and phenanthryl radicals.

The heterocyclic radicals are monocyclic, bicyclic or polycyclic groups comprising one or more hetero atoms generally chosen from O, S and N, optionally in oxidising form (in the case of S and N).

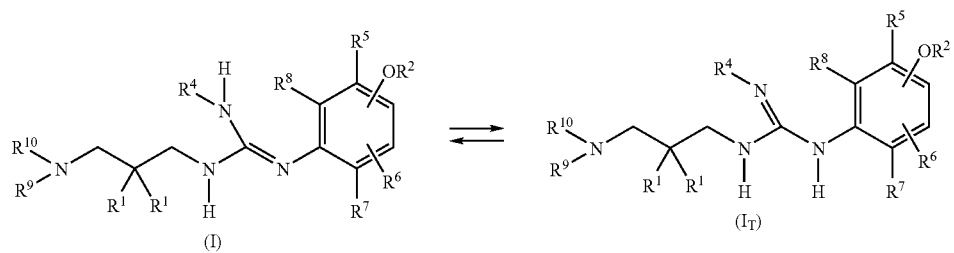

The tautomeric form $(I_T)$ should be understood as forming an integral part of the compounds of the formula (I).

The compounds of the formula (I) above also comprise the prodrugs of these compounds.

The term "prodrugs" means compounds which, once administered to the patient, are chemically and/or biologically converted by the live body into compounds of the formula (I).

In the description hereinbelow, the term "$(C_1-C_{10})$alkyl radical" means a linear or branched hydrocarbon-based chain containing from 1 to 10 carbon atoms, optionally substituted by one or more groups G defined below.

Examples of $(C_1-C_{10})$alkyl radicals are methyl, ethyl, propyl, isopropyl, butyl, isobutyl, tert-butyl, pentyl, isopentyl, neopentyl, methylbutyl, ethylpropyl, hexyl, isohexyl, neohexyl, methylpentyl, dimethylbutyl, ethylbutyl, methylethylpropyl, heptyl, methylhexyl, propylbutyl, dimethylpentyl, Preferably, at least one of the monocycles constituting the heterocycle comprises from 1 to 4 endocyclic hetero atoms and better still from 1 to 3 endocyclic hetero atoms chosen from O, N and S.

According to the invention, the heterocyclic polycyclic nucleus consists of one or more monocycles that are each 5- to 8-membered.

The heterocyclic groups are saturated, partially unsaturated, totally saturated or aromatic.

Examples of 5- to 8-membered monocyclic aromatic heterocyclic groups are heteroaromatic groups derived from pyridine, furan, thiophene, pyrrole, imidazole, thiazole, isoxazole, isothiazole, furazane, pyridazine, pyrimidine, pyrazine, thiazines, oxazole, pyrazole, oxadiazole, triazole and thiadiazole.

Preferred heteroaryl radicals that may be mentioned include pyridyl, pyrimidinyl, triazolyl, thiadiazolyl, oxazolyl, thiazolyl and thienyl radicals.

Examples of bicyclic heteroaryls in which each monocycle is 5- to 8-membered include indolizine, indole, isoindole, benzofuran, benzothiophene, indazole, benzimidazole, benzothiazole, benzofurazane, benzothiofurazane, purine, quinoline, isoquinoline, cinnoline, phthalazine, quinazoline, quinoxaline, naphthyridines, pyrazolotriazine (such as pyrazolo-1,3,4-triazine), pyrazolopyrimidine and pteridine.

Preferred heteroaryl radicals that may be mentioned include quinolyl, pyridyl, benzothiazolyl and triazolyl radicals.

Tricyclic heteroaryls in which each monocycle is 5- to 8-membered are chosen, for example, from acridine, phenazine and carbazole.

The partially or totally saturated heterocyclic groups, or the unsaturated heterocyclic groups, are heterocyclic groups bearing no unsaturations, or comprising one or more unsaturations derived from the aromatic heterocyclic groups defined above, respectively.

Saturated or unsaturated monocyclic 5- to 8-membered heterocycles are the saturated or, respectively, the unsaturated derivatives of the aromatic heterocycles.

More particularly, mention may be made of morpholine, piperidine, thiazolidine, oxazolidine, tetrahydrothienyl, tetrahydrofuranyl, pyrrolidine, isoxazolidine, imidazolidine or pyrazolidine.

The various aryl and heterocyclic groups and radicals defined in the present description are optionally substituted by one or more of the following radicals G:

trifluoromethyl; styryl; a halogen atom; a monocyclic, bicyclic or tricyclic aromatic heterocyclic radical comprising one or more hetero atoms chosen from O, N and S; and optionally substituted by one or more radicals T as defined below; a group Het-CO— in which Het represents an aromatic heterocyclic radical as defined above optionally substituted by one or more radicals T; nitro; cyano; $(C_1-C_{10})$alkyl; $(C_1-C_{10})$alkylcarbonyl; $(C_1-C_{10})$alkoxycarbonyl-A- in which A represents $(C_1-C_6)$alkylene, $(C_2-C_6)$alkenylene or a bond; $(C_3-C_{10})$cycloalkyl; trifluoromethoxy; di$(C_1-C_{10})$alkylamino; $(C_1-C_{10})$alkoxy$(C_1-C_{10})$alkyl; $(C_1-C_{10})$-alkoxy; $(C_6-C_{18})$aryl optionally substituted by one or more radicals T; $(C_6-C_{18})$-aryl$(C_1-C_{10})$alkoxy-$(CO)_n$— in which n is 0 or 1 and aryl is optionally substituted by one or more radicals T; $(C_6-C_{18})$aryloxy$(CO)_n$— in which n is 0 or 1 and in which aryl is optionally substituted by one or more radicals T; $(C_6-C_{18})$arylthio in which aryl is optionally substituted by one or more radicals T; $(C_6-C_{18})$aryloxy-$(C_1-C_{10})$alkyl$(CO)_n$— in which n is 0 or 1 and in which aryl is optionally substituted by one or more radicals T; a saturated or unsaturated, monocyclic 5- to 8-membered heterocycle comprising one or more hetero atoms chosen from O, N and S, optionally substituted by one or more radicals T; $(C_6-C_{18})$arylcarbonyl optionally substituted by one or more radicals T; $(C_6-C_{18})$arylcarbonyl-B—$(CO)_n$— in which n is 0 or 1; B represents $(C_1-C_6)$alkylene or $(C_2-C_6)$alkenylene and aryl is optionally substituted by one or more radicals T; $(C_6-C_{18})$aryl-C—$(CO)_n$— in which n is 0 or 1, C represents $(C_1-C_6)$alkylene or $(C_2-C_6)$alkenylene and aryl is optionally substituted by one or more radicals T; $(C_6-C_{18})$aryl fused to a saturated or unsaturated heterocycle as defined above, optionally substituted by one or more radicals T; $(C_2-C_{10})$alkynyl; T is chosen from a halogen atom; $(C_6-C_{18})$-aryl; $(C_1-C_6)$alkyl; $(C_1-C_6)$alkoxy; $(C_1-C_6)$alkoxy$(C_6-C_{18})$aryl; nitro; carboxyl; $(C_1-C_6)$alkoxycarboxyl; and T may represent oxo in the case where it substitutes a saturated or unsaturated heterocycle; or T represents $(C_1-C_6)$alkoxycarbonyl-$(C_1-C_6)$alkyl; or $(C_1-C_6)$alkylcarbonyl$((C_1-C_6)$alkyl$)_n$— in which n is 0 or 1.

If two vicinal carbon atoms are substituted, T may represent a $C_1-C_6$ alkylenediyl chain or a $C_1-C_6$ alkylenedioxy chain.

The term "halogen atom" means a chlorine, bromine, iodine or fluorine atom.

The term "alkylenediyl chain" means a divalent radical of linear or branched aliphatic hydrocarbon-based type derived from the alkyl groups defined above by abstraction of a hydrogen atom. Preferred examples of alkylenediyl chains are chains —$(CH_2)_k$— in which k represents an integer chosen from 2, 3, 4, 5 and 6 and chains >C$(CH_3)_2$ and —$CH_2$—C$(CH_3)_2$—$CH_2$—. The alkylenedioxy chains denote chains —O—Alk-O— in which Alk represents linear or branched alkylene, it being understood that alkylene is as defined above for alkylenediyl. Preferred meanings of —O—Alk-O— are, for example, —O—C$(CH_3)_2$—O— or —O—$CH_2$—$CH_2$—O—.

The term "alkenylene" is defined as an unsaturated alkylene chain containing one or more ethylenic unsaturations, preferably 1 to 3 ethylenic unsaturations. Examples of alkylene chains are —CH=CH— or —CH=CH—CH=CH—.

The term "alkynyl" means an aliphatic hydrocarbon-based group containing one or more unsaturations of acetylenic type. A preferred example is HC≡C—.

The preferred compounds are those of the formula (I) in which the alkyl radicals optionally present are unsubstituted or monosubstituted, and, in this case, more preferably ω-monosubstituted.

A first preferred subgroup of the compounds of the invention consists of compounds for which $R^8$ represents hydrogen, the other substituents being as defined above.

A second preferred subgroup of the compounds of the invention consists of compounds for which $R^7$ represents hydrogen, the other substituents being as defined above.

A third preferred subgroup of the compounds of the invention consists of compounds for which $R^6$ represents hydrogen, the other substituents being as defined above.

A fourth preferred subgroup of the compounds of the invention consists of compounds for which $R^5$ represents hydrogen, the other substituents being as defined above.

A fifth preferred subgroup of the compounds of the invention consists of compounds for which $R^1$ represents hydrogen or a $(C_1-C_6)$alkyl and preferably $(C_1-C_3)$alkyl radical, more preferably methyl, the other substituents being as defined above.

A sixth even more preferred subgroup of the compounds of the invention consists of compounds for which $R^2$ is chosen from an unsubstituted $(C_1-C_{10})$alkyl radical, an ω-monosubstituted $(C_1-C_{10})$alkyl radical, a $(C_2-C_{10})$alkenyl radical, a $(C_6-C_{18})$aryl$(C_1-C_{10})$alkyl radical, preferably phenyl-$(C_1-C_{10})$alkyl, more preferably benzyl, more preferentially unsubstituted or monosubstituted on the aromatic nucleus, a $(C_1-C_6)$alkyl-O—$(C_1-C_{10})$alkyl radical and a $(C_3-C_{10})$cycloalkyl$(C_1-C_{10})$alkyl radical, preferably $(C_3-C_6)$-cycloalkyl $(C_1-C_{10})$alkyl, the other substituents being as defined above.

A seventh preferred subgroup of the compounds of the invention consists of compounds for which $R^9$ and $R^{10}$ are identical and each represent a hydrogen atom or a $(C_1-C_6)$ alkyl radical, preferably a methyl radical, the other substituents being as defined above.

An eighth preferred subgroup of the compounds of the invention consists of compounds for which $R^3$ and $R^4$ each represent a $(C_1-C_6)$alkyl radical, or $R^3$ represents a hydrogen atom and $R^4$ represents a $(C_1-C_{10})$alkyl radical, or alternatively $R^3$ and $R^4$ form, together with the nitrogen atom that bears them, a 5- or 6-membered heterocycle, the other substituents having the definitions given above.

The compounds of the formula (I) that are also preferred are those having one or more of the following characteristics, taken separately or in combination:

$R^1$ represents a hydrogen atom or a methyl radical;
$R^2$ is chosen from an unsubstituted $(C_1-C_{10})$alkyl radical, an ω-mono-substituted $(C_1-C_{10})$alkyl radical, a $(C_2-C_{10})$alkenyl radical, a phenyl-$(C_1-C_{10})$alkyl radical, preferably benzyl, more preferably unsubstituted or monosubstituted on the aromatic nucleus, a $(C_1-C_6)$alkyl-O—$(C_1-C_{10})$alkyl radical and a $(C_3-C_6)$cycloalkyl $(C_1-C_{10})$alkyl radical;
$R^3$ and $R^4$ each represent a $(C_1-C_6)$alkyl radical, or alternatively $R^3$ represents a hydrogen atom and $R^4$ represents a $(C_1-C_{10})$alkyl radical, or alternatively $R^3$ and $R^4$ form, together with the nitrogen atom that bears them, a 5- or 6-membered heterocycle;
$R^5$ represents hydrogen;
$R^6$ represents hydrogen;
$R^7$ represents hydrogen;
$R^8$ represents hydrogen;
$R^9$ and $R^{10}$, which are identical, each represent a hydrogen atom or a methyl radical.

According to one most particularly preferred embodiment of the present invention, the compounds of the formula (I) are those for which:

$R^1$ represents a hydrogen atom or a methyl radical;
$R^2$ is chosen from an unsubstituted $(C_1-C_{10})$alkyl radical, an ω-mono-substituted $(C_1-C_{10})$alkyl radical, a $(C_2-C_{10})$alkenyl radical, a phenyl-$(C_1-C_{10})$alkyl radical, preferably benzyl, more preferably unsubstituted or monosubstituted on the aromatic nucleus, a $(C_1-C_6)$alkyl-O—$(C_1-C_{10})$alkyl radical and a $(C_3-C_6)$cycloalkyl $(C_1-C_{10})$alkyl radical;
$R^3$ and $R^4$ each represent a $(C_1-C_6)$alkyl radical, or alternatively $R^3$ represents a hydrogen atom and $R^4$ represents a $(C_1-C_{10})$alkyl radical, or alternatively $R^3$ and $R^4$ form, together with the nitrogen atom that bears them, a 5- or 6-membered heterocycle;
$R^5$, $R^6$, $R^7$ and $R^8$ each represent a hydrogen atom; and
$R^9$ and $R^{10}$, which are identical, each represent a hydrogen atom or a methyl radical.

Among the possible substituents (radicals G) for the various radicals $R^1$ to $R^{10}$ of the compounds of the formula (I), the following radicals or groups are preferred:

trifluoromethyl; halogen atom; amino; nitro; cyano; $(C_1-C_{10})$alkyl radical; $(C_2-C_6)$alkynyl radical; $(C_1-C_{10})$alkylcarbonyl radical; $(C_3-C_{10})$cycloalkyl radical; trifluoromethoxy radical; di$(C_1-C_{10})$alkylamino radical; $(C_1-C_{10})$alkoxy-$(C_1-C_{10})$alkyl radical; $(C_1-C_{10})$alkoxy radical; $(C_6-C_{18})$aryl radical optionally substituted by one or more radicals T; $(C_6-C_{18})$aryloxy-$(CO)_n$— radical in which n is 0 or 1 and in which aryl is optionally substituted by one or more radicals T; $(C_6-C_{18})$arylthio radical in which aryl is optionally substituted by one or more radicals T; saturated or unsaturated, monocyclic 5- to 8-membered heterocycle comprising one or more hetero atoms chosen from O, N and S, optionally substituted by one or more radicals T; and $(C_2-C_{10})$alkynyl radical.

More particularly, the preferred compounds of the formula (I) are those chosen from:

N-(3-Amino-2,2-dimethylpropyl)-N'-(4-benzyloxyphenyl)-N"-(3-methylbutyl)guanidine bis(trifluoroacetate);
N-(3-Aminopropyl)-2-methyl-N'-[4-(2-methylbenzyloxy)phenyl]piperidine-1-carboxamidine bis(trifluoroacetate);
N-(3-Aminopropyl)-N'-(3-methylbutyl)-N"-(4-pentyloxyphenyl)guanidine bis(trifluoroacetate);
N-(3-Aminopropyl)-N'-[4-(2-methoxyethoxy)phenyl]-3-methylpiperidine-1-carboxamidine bis(trifluoroacetate);
N-(3-Aminopropyl)-N'-[4-(2-methoxyethoxy)phenyl]-4-methylpiperidine-1-carboxamidine bis(trifluoroacetate);
N'-(3-Aminopropyl)-N-ethyl-N-isopropyl-N"-[4-(2-methoxyethoxy)-phenyl]guanidine bis(trifluoroacetate);
N-(3-Aminopropyl)-4-methyl-N'-[4-(3-methylbutoxy)phenyl]piperidine-1-carboxamidine bis(trifluoroacetate);
N-(3-Aminopropyl)-2-methyl-N'-[4-(3-methylbutoxy)phenyl]piperidine-1-carboxamidine bis(trifluoroacetate);
N-(3-Aminopropyl)-2-ethyl-N'-[4-(3-methylbutoxy)phenyl]piperidine-1-carboxamidine bis(trifluoroacetate);
N'-(3-Aminopropyl)-N-ethyl-N-isopropyl-N"-[4-(3-methylbutoxy)phenyl]-guanidine bis(trifluoroacetate);
N-(3-Aminopropyl)-3-methyl-N'-(4-propoxyphenyl)piperidine-1-carboxamidine bis(trifluoroacetate);
N-(3-Aminopropyl)-4-methyl-N'-(4-propoxyphenyl)piperidine-1-carboxamidine bis(trifluoroacetate);
N-(3-Aminopropyl)-2-methyl-N'-(4-propoxyphenyl)piperidine-1-carboxamidine bis(trifluoroacetate);
N-(3-Aminopropyl)-2-ethyl-N'-(4-propoxyphenyl)piperidine-1-carboxamidine bis(trifluoroacetate);
N'-(3-Aminopropyl)-N-ethyl-N-isopropyl-N"-(4-propoxyphenyl)guanidine bis(trifluoroacetate);
N-(3-Aminopropyl)-N'-[4-(4-tert-butylbenzyloxy)phenyl]-2-methylpiperidine-1-carboxamidine bis(trifluoroacetate);
N-(3-Aminopropyl)-N'-[4-(4-tert-butylbenzyloxy)phenyl]-2-ethylpiperidine-1-carboxamidine bis(trifluoroacetate);
N-(3-Aminopropyl)-4-benzyl-N'-[4-(4,4,4-trifluorobutoxy)phenyl]piperidine-1-carboxamidine bis(trifluoroacetate);
N-(3-Aminopropyl)-2-ethyl-N'-(4-pentyloxyphenyl)piperidine-1-carboxamidine bis(trifluoroacetate); and
N'-(3-Amino-2,2-dimethylpropyl)-N-ethyl-N-isopropyl-N"-[4-(2-methylbenzyloxy)phenyl]guanidine bis(trifluoroacetate).

The invention also relates to pharmaceutical compositions comprising a pharmaceutically effective amount of at least one compound of the formula (I) as defined above in combination with one or more pharmaceutically acceptable vehicles.

These compositions can be administered orally in the form of tablets, gel capsules or granules with immediate release or controlled release, intravenously in the form of an injectable solution, transdermally in the form of an adhesive transdermal device, or locally in the form of a solution, cream or gel.

A solid composition for oral administration is prepared by adding to the active principle a filler and, where appropriate, a binder, a disintegrating agent, a lubricant, a colorant or a flavour enhancer, and by forming the mixture into a tablet, a coated tablet, a granule, a powder or a capsule.

Examples of fillers include lactose, corn starch, sucrose, glucose, sorbitol, crystalline cellulose and silicon dioxide, and examples of binders include poly(vinyl alcohol), poly (vinyl ether), ethylcellulose, methylcellulose, acacia, gum tragacanth, gelatine, shellac, hydroxypropylcellulose, hydroxypropylmethylcellulose, calcium citrate, dextrin and pectin. Examples of lubricants include magnesium stearate, talc, polyethylene glycol, silica and hardened plant oils. The colorant may be any of those permitted for used in medicaments. Examples of flavour enhancers include cocoa powder, mint in herb form, aromatic powder, mint in oil form, borneol and cinnamon powder. Obviously, the tablet or granule can be suitably coated with sugar, gelatine or the like.

An injectable form comprising the compound of the present invention as active principle is prepared, where appropriate, by mixing the said compound with a pH regulator, a buffer agent, a suspension agent, a solubiliser, a stabiliser, an isotonic agent and/or a preserving agent, and by converting the mixture into a form for intravenous, subcutaneous or intramuscular injection, according to a standard process. Where appropriate, the injectable form obtained can be freeze-dried via a standard process.

Examples of suspension agents include methylcellulose, polysorbate 80, hydroxyethylcellulose, acacia, powdered gum tragacanth, sodium carboxymethylcellulose and polyethoxylated sorbitan monolaurate.

Examples of solubilisers include castor oil solidified with polyoxyethylene, polysorbate 80, nicotinamide, polyethoxylated sorbitan monolaurate and the ethyl ester of castor oil fatty acid.

In addition, possible stabilisers include sodium sulfite, sodium metasulfite and ether, while possible preserving agents include methyl p-hydroxybenzoate, ethyl p-hydroxybenzoate, sorbic acid, phenol, cresol and chlorocresol.

The present invention also relates to the use of a compound of the formula (I) of the invention for the preparation of a medicament for the prevention or treatment of dyslipidaemia, atherosclerosis, type II diabetes and related diseases.

The effective administration doses and posologies of the compounds of the invention, intended for the prevention or treatment of a disease, disorder or condition caused by or associated with modulation of CETP activity, depends on a large number of factors, for example on the nature of the inhibitor, the size of the patient, the aim of the desired treatment, the nature of the pathology to be treated, the specific pharmaceutical composition used and the observations and conclusions of the treating physician.

For example, in the case of an oral administration, for example a tablet or a gel capsule, a possible suitable dosage of the compounds of the formula (I) is between about 0.1 mg/kg and about 100 mg/kg of body weight per day, preferably between about 0.5 mg/kg and about 50 mg/kg of body weight per day, more preferably between about 1 mg/kg and about 10 mg/kg of body weight per day and more preferably between about 2 mg/kg and about 5 mg/kg of body weight per day of active material.

If representative body weights of 10 kg and 100 kg are considered in order to illustrate the oral daily dosage range that can be used and as described above, suitable dosages of the compounds of the formula (I) will be between about 1-10 mg and 1000-10 000 mg per day, preferably between about 5-50 mg and 500-5000 mg per day, more preferably between about 10.0-100.0 mg and 100.0-1000.0 mg per day and even more preferably between about 20.0-200.0 mg and about 50.0-500.0 mg per day of active material comprising a preferred compound.

These dosage ranges represent total amounts of active material per day for a given patient. The number of administrations per day at which a dose is administered can vary within wide proportions depending on pharmacokinetic and pharmacological factors, such as the half-life of the active material, which reflects its rate of catabolism and clearance, and also the minimum and optimum levels of the said active material, in blood plasma or in other bodily fluids, which are reached in the patient and which are required for therapeutic efficacy.

Many other factors should also be taken into consideration when determining the number of daily administrations and the amount of active material that should be administered in a single dosage intake. Among these other factors, and not the least of which, is the individual response of the patient to be treated.

The present invention also relates to a general process for the preparation of the compounds of the formula (I) according to the synthetic scheme 1 presented in FIG. 1, in which the various variable substituents are as defined above for the compounds of the formula (I).

According to this process, the aryl thiocyanate (V) is subjected to the action of an amine $HNR^3R^4$, in a polar protic solvent medium, such as an alcohol, for example ethanol, to give, after heating, for example at the reflux point of the solvent, the corresponding thiourea. This thiourea is then placed in a reducing medium, for example in $MnO_4^-$ medium, with the amine of the formula (III), to give the compound of the formula (I), which is isolated and purified, where appropriate.

This process (synthetic route 1) is particularly suitable for the synthesis of the compounds of the formula (I) for which $R^5$, $R^6$, $R^7$ and $R^8$ each represent a hydrogen atom.

According to one variant, the compounds of the formula (I) according to the present invention can also be prepared according to a process involving synthesis on a support, especially on resin.

Figure 2:
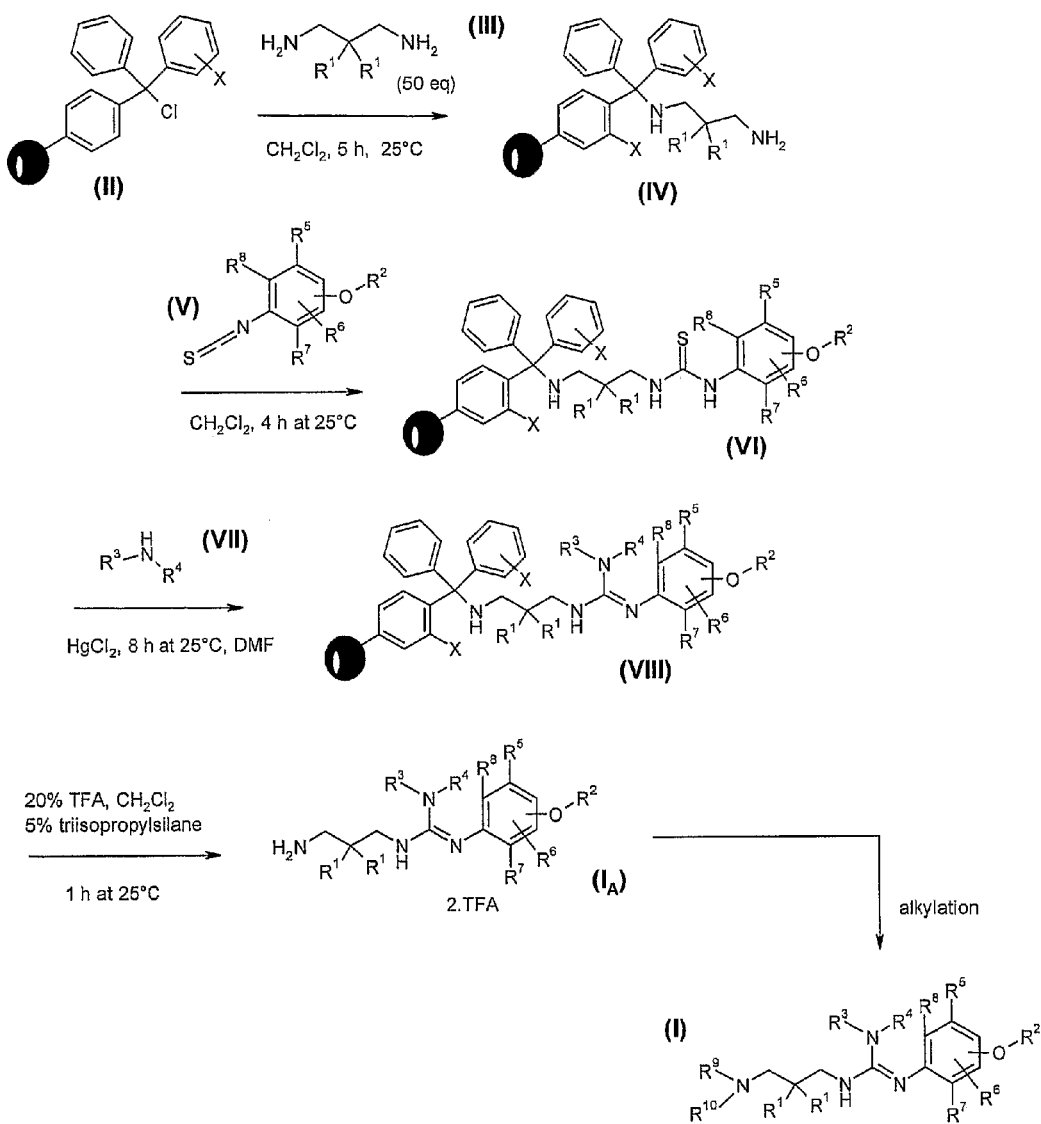

This process is illustrated by scheme 2, presented in FIG. 2, in which scheme:

the compound of the formula (II), in which:

 represents a graft on resin, for example of Bromo Wang type;

X is chosen from a hydrogen atom, a halogen atom, a $(C_1-C_6)$alkyl radical and a $(C_1-C_6)$alkoxy radical;

is placed in contact with an excess of the amine of the formula (III) in an apolar aprotic solvent, for example dichloromethane, generally at room temperature, to give the compound of the formula (IV);

the compound of the formula (IV) is then reacted, under conditions similar to those described above, with a compound of the formula (V), to give the thiourea of the formula (VI);

the said thiourea (VI) is converted, by the action of an amine of the formula (VII), generally at room temperature, in a polar aprotic medium, for example DMF, and in the presence of mercuric salts, for example $HgCl_2$, to give the guanidine of the formula (VIII);

the guanidine (VIII) is then detached from the resin, according to any technique known per se, for example using trifluoroacetic acid, dichloromethane and triisopropylsilane, to give the compounds of the formula ($I_A$), which are a special case of the compounds of the formula (I) for which $R^9$ and $R^{10}$ each represent a hydrogen atom;

and the terminal amine of these compounds of the formula ($I_A$) can optionally be selectively mono- or dialkylated according to standard amine alkylation techniques that are well known to those skilled in the art.

In the processes described above, it should be understood that the operating conditions can vary substantially depending on the various substituents present in the compounds of the formula (I) that it is desired to prepare. Such variations and adaptations are readily accessible to a person skilled in the art, for example from scientific reviews, the patent literature, Chemical Abstracts, and computer databases, including the Internet Similarly, the starting materials are either commercially available or are accessible via syntheses that a person skilled in the art can readily find, for example in the various publications and databases described above.

Figure 3:
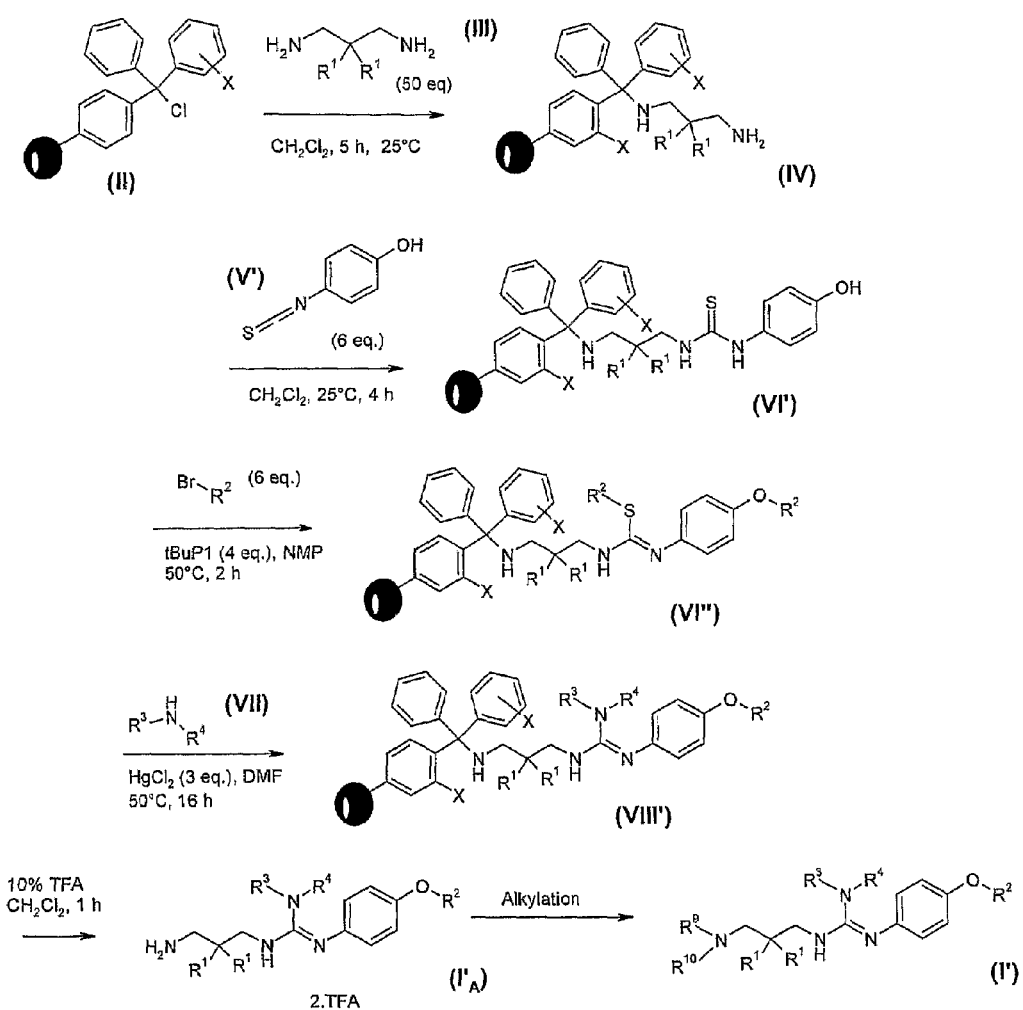

By way of example of a variant of the process described above, the compounds of the general formula (I), for which $R^5$, $R^6$, $R^7$ and $R^8$ each represent a hydrogen atom, can advantageously be prepared according to the synthetic scheme 3 presented in FIG. 3.

The possible optical isomers of the compounds of the formula (I) can be obtained on the one hand via standard techniques for separating and/or purifying isomers known to those skilled in the art, from the racemic mixture of the compound of the formula (I). The optical isomers can also be obtained directly via stereoselective synthesis of an optically active starting compound.

The examples that follow illustrate the present invention without limiting it in any way. In these examples and in the proton nuclear magnetic resonance data (300 MHz NMR), the following abbreviations have been used: s for singlet, d for doublet, t for triplet, q for quartet, o for octet, m for complex multiplet and b for broad. The chemical shifts δ are expressed in ppm, unless otherwise indicated. TFA means trifluoroacetic acid.

EXAMPLES

Example 1

N-(4-benzyloxyphenyl)-N'-(3-dimethylamino-2,2-dimethylpropyl)-N''-(3-methylbutyl)guanidine (Synthetic Scheme 1)

Step a): N-(4-benzyloxyphenyl)-N'-(3-methylbutyl)thiourea

A suspension of 4-benzyloxyphenyl isothiocyanate (2 g) in ethanol (10 ml) is maintained at reflux until dissolution is complete. 3-Methylbutylamine (0.72 g; 1 eq.) is then added in a single portion. The reaction medium is refluxed for 3 hours. After cooling, the mixture is taken up in water and the white precipitate is then filtered off by suction and dried. After purification by chromatography on silica (eluent: dichloromethane), 2 g of N-(4-benzyloxyphenyl)-N'-(3-methylbutyl)thiourea are obtained.

$^1$H NMR (300 MHz, CDCl$_3$) δ: 0.83 ppm (6H, d, J=6.6 Hz); 1.34 ppm (2H, m); 1.50 ppm (1H, m); 3.54 ppm (2H, m); 5.00 ppm (2H, s); 5.70 ppm (1H, bs); 6.94 ppm (2H, d, J=9.0 Hz); 7.06 ppm (2H, d, J=9.0 Hz); 7.33 ppm (5H, m); 7.48 ppm (1H, bs).

Step b): N-(4-benzyloxyphenyl)-N'-(3-dimethylamino-2,2-dimethylpropyl)-N''-(3-methylbutyl)guanidine Benzyltriethylammonium permanganate (0.281 g; 1.5 eq.) is added, at 5° C. and portionwise, to a solution of N-(4-benzyloxyphenyl)-N'-(3-methylbutyl)thiourea (0.200 g) and 3-dimethylamino-2,2-dimethylpropylamine (0.156 g; 2 eq.) in tetrahydrofuran (THF; 2.2 ml). The reaction medium is stirred for three days at room temperature. After filtration and concentration, the product is purified by chromatography on silica (eluent: methanol +0.1% acetic acid). The product, dissolved in dichloromethane, is washed with 1N sodium hydroxide. After drying and concentration, 0.067 g of N-(4-benzyloxyphenyl)-N'-(3-dimethylamino-2,2-dimethylpropyl)-N''-(3-methylbutyl)guanidine is obtained.

MS: 425.4 (M+H$^+$) $^1$H NMR (300 MHz, CDCl$_3$) δ: 0.84 ppm (12H, m); 1.33 ppm (4H, m); 1.52 ppm (4H, bm); 2.18 ppm (6H, m); 3.03 ppm (3H, bm); 4.95 ppm (2H, s); 6.75 ppm (2H, d, J=9.0 Hz); 6.82 ppm (2H, d, J=9.0 Hz); 7.33 ppm (5H, m).

Examples A

General Procedure for the Preparation of the N'-(3-aminopropyl)-N''-(benzyloxyphenyl)-N,N-dialkylguanidine compounds (Synthetic Scheme 2)

Step a): General Procedure for the Preparation of the 1,3-propanediamine Resins

2-Chlorotrityl chloride resin (25 g, 1 eq.) is added, in four portions at intervals of one hour, to a solution of 1,3-propanediamine (147 g, 50 eq.) in dichloromethane (1 l). After stirring for a further one hour at room temperature, methanol (500 ml) is added and stirring is continued for 20 minutes. The resin is filtered off and then washed with methanol (3×350 ml), a ¼ TEA/DMF (triethanolamine/dimethylformamide) mixture, methanol (MeOH; 3×350 ml) and dichloromethane (3×350 ml). The resin is then dried under vacuum, Step b): General Procedure for the Preparation of the N-(3-aminopropyl)-N'-(benzyloxyphenyl)thiourea Resins A 0.24 M solution of benzyloxyphenyl isothiocyanate in dichloromethane (4.5 ml; 6 eq.) is added to a reactor containing the 1,3-propanediamine resin (180 μmol; 1 eq.). The suspension is stirred for 4 hours at room temperature. The resin is then washed with dichloromethane (3×5 ml) and N-methylpyrrolidone (NMP; 3×5 ml). The resin is stored as a suspension in NMP (1 ml) and then used in the following reaction.

Step c): General Procedure for the Preparation of the N'-(3-aminopropyl)-N''-(benzyloxyphenyl)-N,N-dialkylguanidine Resins The suspension of N-(3-aminopropyl)-N'-(benzyloxyphenyl)thiourea resin in dimethylformamide (DMF; 1 ml) is treated with a 0.72 M solution of amine in DMF (1 ml; 6 eq.) and with a 0.72 M solution of mercuric chloride in DMF (1 ml; 6 eq.). The reaction is stirred for 8 hours at 25° C. The resin is then washed with a thiocarbamate solution in a mixture of THF/water solvents (2×5 ml), with DMF (3×5 ml), methanol (3×5 ml) and dichloromethane (3×5 ml). The resin, stored as a suspension in dichloromethane (1 ml), is then used in the following reaction.

Step d): General Procedure for the Preparation of the N'-(3-aminopropyl)-N''-(benzyloxyphenyl)-N,N-dialkylguanidine Compounds The suspension of N'-(3-aminopropyl)-N''-(benzyloxyphenyl)-N,N-dialkylguanidine resin in dichloromethane (1 ml) is treated with a solution of 40% trifluoroacetic acid (TFA) and 10% triisopropylsilane in dichloromethane (1 ml). The reaction is stirred for 1 hour at room temperature and is then filtered and the filtrate is concentrated in a centrifuge under vacuum to give the compound N'-(3-aminopropyl)-N''-(benzyloxyphenyl)-N,N-dialkylguanidine in the form of the di-TFA salt.

The compounds of Examples 2-16 below were obtained according to the procedure described above.

Example 2

N-(3-Amino-2,2-dimethylpropyl)-N'-(3-benzyloxyphenyl)-N''-(3-methylbutyl)-guanidine Salt: TFA×2
Mass: ES+ 397.5

Example 3

N-(3-Amino-2,2-dimethylpropyl)-N'-(4-benzyloxyphenyl)-3-hydroxymethylpiperidine-1-carboxamidine Salt: TFA×2
Mass: ES+ 425.5

Example 4

N-(3-Amino-2,2-dimethylpropyl)-N'-(4-benzyloxyphenyl)pyrrolidine-1-carboxamidine Salt: TFA×2
Mass: ES+ 381.5

Example 5

N-(3-Amino-2,2-dimethylpropyl)-N'-(4-benzyloxyphenyl)-N''-(3-methylbutyl)-guanidine Salt: TFA×2
Mass: ES+ 397.5

Example 6

N-(3-Aminopropyl)-N'-(3-benzyloxyphenyl)pyrrolidine-1-carboxamidine

Salt: TFA×2
Mass: ES+ 353.4

Example 7

N-(3-Aminopropyl)-N'-(4-benzyloxyphenyl)-N''-phenethylguanidine

Salt: TFA×2
Mass: ES+ 403.5

Example 8

N-(3-Aminopropyl)-N'-(3-benzyloxyphenyl)-N''-(3-methylbutyl)guanidine

Salt: TFA×2
Mass: ES+ 369.3

Example 9

N-(3-Aminopropyl)-N'-(3-benzyloxyphenyl)-3-hydroxymethylpiperidine-1-carboxamidine Salt: TFA×2
Mass: ES+ 397.3

Example 10

N-(3-Aminopropyl)-N'-(4-benzyloxyphenyl)pyrrolidine-1-carboxamidine

Salt: TFA×2
Mass: ES+ 353.3

Example 11

N-(3-Aminopropyl)-N'-(4-benzyloxyphenyl)-3-hydroxymethylpiperidine-1-carboxamidine Salt: TFA×2
Mass: ES+ 397.3

Example 12

N-(3-Aminopropyl)-N'-(4-benzyloxyphenyl)-N''-(3-methylbutyl)guanidine

Salt: TFA×2
Mass: ES+ 369.3

Example 13

N-(3-Amino-2,2-dimethylpropyl)-N'-(3-benzyloxyphenyl)-3-hydroxymethylpiperidine-1-carboxamidine Salt: TFA×2
Mass: ES+ 425.4

Example 14

N-(3-Amino-2,2-dimethylpropyl)-N'-(3-benzyloxyphenyl)pyrrolidine-1-carboxamidine Salt: TFA×2
Mass: ES+ 381.4

Example 15

N-(3-Aminopropyl)-N'-(4-benzyloxyphenyl)-2-methylpiperidine-1-carboxamidine

Salt: TFA×2
Mass: ES+ 381.4

Example 16

N-(3-Aminopropyl)-N'-(3-benzyloxyphenyl)-2-methylpiperidine-1-carboxamidine

Salt: TFA×2
Mass: ES+ 381.4

Examples B

General Procedure for the Preparation of the N'-(3-aminopropyl)-N''-(benzyloxyphenyl)-N,N-dialkylguanidine compounds (Synthetic Scheme 3)
Step a): General Procedure for the Preparation of the N-(3-aminopropyl)-N'-(4-hydroxyphenyl)thiourea Resins A 0.24 M solution of hydroxyphenyl isothiocyanate in dichloromethane (4.5 ml; 6 eq.) is added to a reactor containing the diaminoalkyl resin (180 μmol; 1 eq.). The suspension is stirred for 4 hours at room temperature. The resin is then washed with dichloromethane (3×5 ml) and NMP (3×5 ml). The resin, stored as a suspension in NMP (1 ml), is then used in the following reaction.

Step b): General Procedure for the Preparation of the N-(3-aminopropyl)-N'-(4-alkoxyphenyl)-S-alkylisothiourea Resins The suspension of N-(3-aminopropyl)-N'-(4-hydroxyphenyl)thiourea resin in NMP (1 ml) is treated with a 0.48 M solution of phosphazene base tBuP1 in NMP (1.5 ml; 4 eq.) and with a 0.72 M solution of alkyl halide in NMP (1.5 ml; 6 eq.). The reaction is stirred for 2 hours at 50° C. The resin is then washed with methanol (3×5 ml), THF (3×5 ml), dichloromethane (3×5 ml) and DMF (3×5 ml). The resin, stored as a suspension in DMF (1 ml), is then used in the following reaction.

Step c): General Procedure for the Preparation of the N'-(3-aminopropyl)-N''-(4-alkoxyphenyl)-N,N-dialkylguanidine Resins The suspension of N-(3-aminopropyl)-N'-(4-alkoxyphenyl)-S-alkylisothiourea resin in DMF (1 ml) is treated with a 0.39 M solution of amine in DMF (1.4 ml; 3 eq.) and with a 0.36 M solution of mercuric chloride in DMF (1.5 ml; 3 eq.). The reaction is stirred for 16 hours at 50° C. The resin is then washed with a solution of thiocarbamate in a mixture of THF/water solvents (2×5 ml), with DMF (3×5 ml), methanol (3×5 ml) and dichloromethane (3×5 ml). The resin, stored as a suspension in dichloromethane (1 ml), is then used in the following reaction.

Step d): General Procedure for the Preparation of the N'-(3-aminopropyl)-N''-(4-alkoxyphenyl)-N,N-dialkylguanidine Compounds The suspension of N'-(3-aminopropyl)-N''-(4-alkoxyphenyl)-N,N-dialkylguanidine resin in dichloromethane (1 ml) is treated with a 20% solution of TFA in dichloromethane (1 ml). The reaction is stirred for 1 hour at room temperature. The reaction is then filtered and the filtrate is concentrated in a centrifuge under vacuum to give the N'-(3-aminopropyl)-N''-(4-alkoxyphenyl)-N,N-dialkylguanidine compound in the form of the di-TFA salt.

The compounds of Examples 17-198 below were obtained according to the procedure described above.

Example 17

N-(3-Aminopropyl)-2-methyl-N'-[4-(4-trifluoromethylbenzyloxy)phenyl]-piperidine-1-carboxamidine Salt: TFA×2
Mass: ES+ 449.4

Example 18

N-(3-Aminopropyl)-2-methyl-N'-[4-(2-methylbenzyloxy)phenyl]piperidine-1-carboxamidine Salt: TFA×2
Mass: ES+ 395.5

Example 19

N-(3-Aminopropyl)-2-methyl-N'-(4-pentyloxyphenyl)piperidine-1-carboxamidine

Salt: TFA×2
Mass: ES+ 361.4

Example 20

N-(3-Aminopropyl)-N'-(3-methylbutyl)-N''-(4-pentyloxyphenyl)guanidine

Salt: TFA×2
Mass: ES+ 349.4

Example 21

N-(3-Aminopropyl)-N'-[4-(2-methylbenzyloxy)phenyl]-N''-(3-methylbutyl)guanidine

Salt: TFA×2
Mass: ES+ 383.3

Example 22

N-(3-Aminopropyl)-N'-(3-methylbutyl)-N''-[4-(4-trifluoromethylbenzyloxy)-phenyl]guanidine Salt: TFA×2
Mass: ES+ 437.4

Example 23

N-(3-Aminopropyl)-4-benzyl-N'-[4-(4-methylbenzyloxy)phenyl]piperidine-1-carboxamidine Salt: TFA×2
Mass: ES+ 471.3

Example 24

N-(3-Aminopropyl)-3-methyl-N'-[4-(4-methylbenzyloxy)phenyl]piperidine-1-carboxamidine Salt: TFA×2
Mass: ES+ 395.3

Example 25

N-(3-Aminopropyl)-4-methyl-N'-[4-(4-methylbenzyloxy)phenyl]piperidine-1-carboxamidine Salt: TFA×2
Mass: ES+ 395.4

Example 26

N-(3-Aminopropyl)-2-methyl-N'-[4-(4-methylbenzyloxy)phenyl]piperidine-1-carboxamidine Salt: TFA×2
Mass: ES+ 395.4

Example 27

N-(3-Aminopropyl)-2-ethyl-N'-[4-(4-methylbenzyloxy)phenyl]piperidine-1-carboxamidine Salt: TFA×2
Mass: ES+ 409.4

Example 28

N'-(3-Aminopropyl)-N-ethyl-N-isopropyl-N''-[4-(4-methylbenzyloxy)phenyl]-guanidine Salt: TFA×2
Mass: ES+ 383.4

Example 29

N-(3-Aminopropyl)-4-benzyl-N'-[4-(2-methoxyethoxy)phenyl]piperidine-1-carboxamidine Salt: TFA×2
Mass: ES+ 425.4

Example 30

N-(3-Aminopropyl)-N'-[4-(2-methoxyethoxy)phenyl]-3-methylpiperidine-1-carboxamidine Salt: TFA×2
Mass: ES+ 349.3

Example 31

N-(3-Aminopropyl)-N'-[4-(2-methoxyethoxy)phenyl]-4-methylpiperidine-1-carboxamidine Salt: TFA×2
Mass: ES+ 349.3

Example 32

N'-(3-Aminopropyl)-N-ethyl-N-isopropyl-N''-[4-(2-methoxyethoxy)phenyl]guanidine

Salt: TFA×2
Mass: ES+ 337.3

Example 33

N-(3-Aminopropyl)-2-methyl-N'-[4-(3-methylbut-2-enyloxy)phenyl]piperidine-1-carboxamidine Salt: TFA×2
Mass: ES+ 359.4

Example 34

N'-(3-Aminopropyl)-N-ethyl-N-isopropyl-N''-[4-(3-methylbut-2-enyloxy)phenyl]-guanidine Salt: TFA×2
Mass: ES+ 347.4

Example 35

N-(3-Aminopropyl)-4-benzyl-N'-[4-(3-methylbutoxy)phenyl]piperidine-1-carboxamidine Salt: TFA×2
Mass: ES+ 437.4

Example 36

N-(3-Aminopropyl)-4-methyl-N'-[4-(3-methylbutoxy)phenyl]piperidine-1-carboxamidine Salt: TFA×2
Mass: ES+ 361.4

Example 37

N-(3-Aminopropyl)-2-methyl-N'-[4-(3-methylbutoxy)phenyl]piperidine-1-carboxamidine Salt: TFA×2
Mass: ES+ 361.4

Example 38

N-(3-Aminopropyl)-2-ethyl-N'-[4-(3-methylbutoxy)phenyl]piperidine-1-carboxamidine Salt: TFA×2
Mass: ES+ 375.4

Example 39

N'-(3-Aminopropyl)-N-ethyl-N-isopropyl-N''-[4-(3-methylbutoxy)phenyl]guanidine

Salt: TFA×2
Mass: ES+ 349.4

Example 40

N-(3-Aminopropyl)-4-benzyl-N'-(4-decyloxyphenyl)piperidine-1-carboxamidine

Salt: TFA×2
Mass: ES+ 507.5

Example 41

N-(3-Aminopropyl)-N'-(4-decyloxyphenyl)-3-methylpiperidine-1-carboxamidine

Salt: TFA×2
Mass: ES+ 431.4

Example 42

N-(3-Aminopropyl)-N'-(4-decyloxyphenyl)-4-methylpiperidine-1-carboxamidine

Salt: TFA×2
Mass: ES+ 431.5

Example 43

N-(3-Aminopropyl)-N'-(4-decyloxyphenyl)-2-methylpiperidine-1-carboxamidine

Salt: TFA×2
Mass: ES+ 431.4

Example 44

N-(3-Aminopropyl)-N'-(4-decyloxyphenyl)-2-ethylpiperidine-1-carboxamidine

Salt: TFA×2
Mass: ES+ 445.5

Example 45

N'-(3-Aminopropyl)-N''-(4-decyloxyphenyl)-N-ethyl-N-isopropylguanidine

Salt: TFA×2
Mass: ES+ 419.5

Example 46

N-(3-Aminopropyl)-4-benzyl-N'-(4-propoxyphenyl)piperidine-1-carboxamidine

Salt: TFA×2
Mass: ES+ 409.4

Example 47

N-(3-Aminopropyl)-3-methyl-N'-(4-propoxyphenyl)piperidine-1-carboxamidine

Salt: TFA×2
Mass: ES+ 333.3

Example 48

N-(3-Aminopropyl)-4-methyl-N'-(4-propoxyphenyl)piperidine-1-carboxamidine

Salt: TFA×2
Mass: ES+ 333.3

Example 49

N-(3-Aminopropyl)-2-methyl-N'-(4-propoxyphenyl)piperidine-1-carboxamidine

Salt: TFA×2
Mass: ES+ 333.3

Example 50

N-(3-Aminopropyl)-2-ethyl-N'-(4-propoxyphenyl)piperidine-1-carboxamidine

Salt: TFA×2
Mass: ES+ 347.4

Example 51

N'-(3-Aminopropyl)-N-ethyl-N-isopropyl-N''-(4-propoxyphenyl)guanidine

Salt: TFA×2
Mass: ES+ 321.4

Example 52

N-(3-Aminopropyl)-4-benzyl-N'-[4-(5-methylhexyloxy)phenyl]piperidine-1-carboxamidine Salt: TFA×2
Mass: ES+ 465.4

Example 53

N-(3-Aminopropyl)-3-methyl-N'-[4-(5-methylhexyloxy)phenyl]piperidine-1-carboxamidine Salt: TFA×2
Mass: ES+ 389.4

Example 54

N-(3-Aminopropyl)-4-methyl-N'-[4-(5-methylhexyloxy)phenyl]piperidine-1-carboxamidine Salt: TFA×2
Mass: ES+ 389.4

Example 55

N-(3-Aminopropyl)-2-methyl-N'-[4-(5-methylhexyloxy)phenyl]piperidine-1-carboxamidine Salt: TFA×2
Mass: ES+ 389.4

Example 56

N-(3-Aminopropyl)-2-ethyl-N'-[4-(5-methylhexyloxy)phenyl]piperidine-1-carboxamidine Salt: TFA×2
Mass: ES+ 403.4

Example 57

N'-(3-Aminopropyl)-N-ethyl-N-isopropyl-N''-[4-(5-methylhexyloxy)phenyl]guanidine Salt: TFA×2
Mass: ES+ 377.4

Example 58

N-(3-Aminopropyl)-N'-[4-(4-tert-butylbenzyloxy)phenyl]-3-methylpiperidine-1-carboxamidine Salt: TFA×2
Mass: ES+ 437.4

Example 59

N-(3-Aminopropyl)-N'-[4-(4-tert-butylbenzyloxy)
phenyl]-4-methylpiperidine-1-carboxamidine Salt: TFA×2
Mass: ES+ 437.4

Example 60

N-(3-Aminopropyl)-N'-[4-(4-tert-butylbenzyloxy)
phenyl]-2-methylpiperidine-1-carboxamidine Salt: TFA×2
Mass: ES+ 437.4

Example 61

N-(3-Aminopropyl)-N'-[4-(4-tert-butylbenzyloxy)
phenyl]-2-ethylpiperidine-1-carboxamidine Salt: TFA×2
Mass: ES+ 451.4

Example 62

N-(3-Aminopropyl)-4-benzyl-N'-[4-(4-cyanobenzy-
loxy)phenyl]piperidine-1-carboxamidine Salt: TFA×2
Mass: ES+ 482.3

Example 63

N-(3-Aminopropyl)-N'-[4-(4-cyanobenzyloxy)phe-
nyl]-3-methylpiperidine-1-carboxamidine Salt: TFA×2
Mass: ES+ 406.3

Example 64

N-(3-Aminopropyl)-N'-[4-(4-cyanobenzyloxy)phe-
nyl]-4-methylpiperidine-1-carboxamidine Salt: TFA×2
Mass: ES+ 406.3

Example 65

N-(3-Aminopropyl)-N'-[4-(4-cyanobenzyloxy)phe-
nyl]-2-methylpiperidine-1-carboxamidine Salt: TFA×2
Mass: ES+ 406.3

Example 66

N-(3-Aminopropyl)-N'-[4-(4-cyanobenzyloxy)phe-
nyl]-2-ethylpiperidine-1-carboxamidine Salt: TFA×2
Mass: ES+ 420.4

Example 67

N'-(3-Aminopropyl)-N''-[4-(4-cyanobenzyloxy)phe-
nyl]-N-ethyl-N-isopropyl-guanidine Salt: TFA×2
Mass: ES+ 394.3

Example 68

N-(3-Aminopropyl)-4-benzyl-N'-[4-(2-cyanobenzy-
loxy)phenyl]piperidine-1-carboxamidine Salt: TFA×2
Mass: ES+ 482.3

Example 69

N-(3-Aminopropyl)-N'-[4-(2-cyanobenzyloxy)phe-
nyl]-3-methylpiperidine-1-carboxamidine Salt: TFA×2
Mass: ES+ 406.3

Example 70

N-(3-Aminopropyl)-N'-[4-(2-cyanobenzyloxy)phe-
nyl]-4-methylpiperidine-1-carboxamidine Salt: TFA×2
Mass: ES+ 406.3

Example 71

N-(3-Aminopropyl)-N'-[4-(2-cyanobenzyloxy)phe-
nyl]-2-methylpiperidine-1-carboxamidine Salt: TFA×2
Mass: ES+ 406.3

Example 72

N-(3-Aminopropyl)-N'-[4-(2-cyanobenzyloxy)phe-
nyl]-2-ethylpiperidine-1-carboxamidine Salt: TFA×2
Mass: ES+ 420.3

Example 73

N-(3-Aminopropyl)-N'-[4-(2-cyclohexylethoxy)phe-
nyl]-3-methylpiperidine-1-carboxamidine Salt: TFA×2
Mass: ES+ 401.4

Example 74

N-(3-Aminopropyl)-N'-[4-(2-cyclohexylethoxy)phe-
nyl]-4-methylpiperidine-1-carboxamidine Salt: TFA×2
Mass: ES+ 401.4

Example 75

N-(3-Aminopropyl)-N'-[4-(2-cyclohexylethoxy)phenyl]-2-methylpiperidine-1-carboxamidine Salt: TFA×2
Mass: ES+ 401.4

Example 76

N-(3-Aminopropyl)-N'-[4-(2-cyclohexylethoxy)phenyl]-2-ethylpiperidine-1-carboxamidine Salt: TFA×2
Mass: ES+ 415.4

Example 77

N'-(3-Aminopropyl)-N''-[4-(2-cyclohexylethoxy)phenyl]-N-ethyl-N-isopropyl-guanidine Salt: TFA×2
Mass: ES+ 389.4

Example 78

N-(3-Aminopropyl)-4-benzyl-N'-[4-(3-cyanopropoxy)phenyl]piperidine-1-carboxamidine Salt: TFA×2
Mass: ES+ 434.3

Example 79

N-(3-Aminopropyl)-N'-[4-(3-cyanopropoxy)phenyl]-3-methylpiperidine-1-carboxamidine Salt: TFA×2
Mass: ES+ 358.3

Example 80

N-(3-Aminopropyl)-N'-[4-(3-cyanopropoxy)phenyl]-4-methylpiperidine-1-carboxamidine Salt: TFA×2
Mass: ES+ 358.2

Example 81

N-(3-Aminopropyl)-N'-[4-(3-cyanopropoxy)phenyl]-2-methylpiperidine-1-carboxamidine Salt: TFA×2
Mass: ES+ 358.2

Example 82

N-(3-Aminopropyl)-N'-[4-(3-cyanopropoxy)phenyl]-2-ethylpiperidine-1-carboxamidine Salt: TFA×2
Mass: ES+ 372.3

Example 83

N'-(3-Aminopropyl)-N''-[4-(3-cyanopropoxy)phenyl]-N ethyl-N-isopropyl-guanidine

Salt: TFA×2
Mass: ES+ 346.3

Example 84

N-(3-Aminopropyl)-4-benzyl-N'-[4-(2-methylbenzyloxy)phenyl]piperidine-1-carboxamidine Salt: TFA×2
Mass: ES+ 471.4

Example 85

N-(3-Aminopropyl)-3-methyl-N'-[4-(2-methylbenzyloxy)phenyl]piperidine-1-carboxamidine Salt: TFA×2
Mass: ES+ 395.4

Example 86

N-(3-Aminopropyl)-4-methyl-N'-[4-(2-methylbenzyloxy)phenyl]piperidine-1-carboxamidine Salt: TFA×2
Mass: ES+ 395.3

Example 87

N-(3-Aminopropyl)-2-ethyl-N'-[4-(2-methylbenzyloxy)phenyl]piperidine-1-carboxamidine Salt: TFA×2
Mass: ES+ 409.4

Example 88

N'-(3-Aminopropyl)-N-ethyl-N-isopropyl-N''-[4-(2-methylbenzyloxy)phenyl]-guanidine Salt: TFA×2
Mass: ES+ 383.4

Example 89

N-(3-Aminopropyl)-4-benzyl-N'-[4-(3-trifluoromethoxybenzyloxy)phenyl]-piperidine-1-carboxamidine Salt: TFA×2
Mass: ES+ 541.3

Example 90

N-(3-Aminopropyl)-3-methyl-N'-[4-(3-trifluoromethoxybenzyloxy)phenyl]-piperidine-1-carboxamidine Salt: TFA×2
Mass: ES+ 465.3

Example 91

N-(3-Aminopropyl)-4-methyl-N'-[4-(3-trifluoromethoxybenzyloxy)phenyl]-piperidine-1-carboxamidine Salt: TFA×2
Mass: ES+ 465.3

Example 92

N-(3-Aminopropyl)-2-methyl-N'-[4-(3-trifluoromethoxybenzyloxy)phenyl]-piperidine-1-carboxamidine Salt: TFA×2
Mass: ES+ 465.3

Example 93

N-(3-Aminopropyl)-2-ethyl-N'-[4-(3-trifluoromethoxybenzyloxy)phenyl]-piperidine-1-carboxamidine Salt: TFA×2
Mass: ES+ 479.3

Example 94

N'-(3-Aminopropyl)-N-ethyl-N-isopropyl-N"-[4-(3-trifluoromethoxybenzyloxy)-phenyl]guanidine Salt: TFA×2
Mass: ES+ 453.3

Example 95

N-(3-Aminopropyl)-4-benzyl-N'-[4-(4,4,4-trifluorobutoxy)phenyl]piperidine-1-carboxamidine Salt: TFA×2
Mass: ES+ 477.3

Example 96

N-(3-Aminopropyl)-3-methyl-N'-[4-(4,4,4-trifluorobutoxy)phenyl]piperidine-1-carboxamidine Salt: TFA×2
Mass: ES+ 401.3

Example 97

N-(3-Aminopropyl)-4-methyl-N'-[4-(4,4,4-trifluorobutoxy)phenyl]piperidine-1-carboxamidine Salt: TFA×2
Mass: ES+ 401.3

Example 98

N-(3-Aminopropyl)-2-methyl-N'-[4-(4,4,4-trifluorobutoxy)phenyl]piperidine-1-carboxamidine Salt: TFA×2
Mass: ES+ 401.3

Example 99

N-(3-Aminopropyl)-2-ethyl-N'-[4-(4,4,4-trifluorobutoxy)phenyl]piperidine-1-carboxamidine Salt: TFA×2
Mass: ES+ 415.3

Example 100

N'-(3-Aminopropyl)-N-ethyl-N-isopropyl-N"-[4-(4,4,4-trifluorobutoxy)phenyl]-guanidine Salt: TFA×2
Mass: ES+ 389.3

Example 101

N-(3-Aminopropyl)-4-benzyl-N'-(4-pentyloxyphenyl)piperidine-1-carboxamidine

Salt: TFA×2
Mass: ES+ 437.4

Example 102

N-(3-Aminopropyl)-3-methyl-N'-(4-pentyloxyphenyl)piperidine-1-carboxamidine

Salt: TFA×2
Mass: ES+ 361.4

Example 103

N-(3-Aminopropyl)-4-methyl-N'-(4-pentyloxyphenyl)piperidine-1-carboxamidine

Salt: TFA×2
Mass: ES+ 361.4

Example 104

N-(3-Aminopropyl)-2-ethyl-N'-(4-pentyloxyphenyl)piperidine-1-carboxamidine

Salt: TFA×2
Mass: ES+ 375.4

Example 105

N'-(3-Aminopropyl)-N-ethyl-N-isopropyl-N"-(4-pentyloxyphenyl)guanidine

Salt: TFA×2
Mass: ES+ 349.4

Example 106

N-(3-Aminopropyl)-4-benzyl-N'-[4-(4-methanesulfonylbenzyloxy)phenyl]-piperidine-1-carboxamidine Salt: TFA×2
Mass: ES+ 535.3

Example 107

N-(3-Aminopropyl)-N'-[4-(4-methanesulfonylbenzyloxy)phenyl]-3-methylpiperidine-1-carboxamidine Salt: TFA×2
Mass: ES+ 459.3

Example 108

N-(3-Aminopropyl)-N'-[4-(4-methanesulfonylbenzyloxy)phenyl]-4-methylpiperidine-1-carboxamidine Salt: TFA×2
Mass: ES+ 459.3

Example 109

N-(3-Aminopropyl)-N'-[4-(4-methanesulfonylbenzyloxy)phenyl]-2-methylpiperidine-1-carboxamidine Salt: TFA×2
Mass: ES+ 459.3

Example 110

N-(3-Aminopropyl)-2-ethyl-N'-[4-(4-methanesulfonylbenzyloxy)phenyl]-piperidine-1-carboxamidine Salt: TFA×2
Mass: ES+ 473.3

Example 111

N'-(3-Aminopropyl)-N-ethyl-N-isopropyl-N''-[4-(4-methanesulfonylbenzyloxy)-phenyl]guanidine Salt: TFA×2
Mass: ES+ 447.3

Example 112

N-(3-Aminopropyl)-4-benzyl-N'-[4-(4-trifluoromethoxybenzyloxy)phenyl]-piperidine-1-carboxamidine Salt: TFA×2
Mass: ES+ 541.3

Example 113

N-(3-Aminopropyl)-3-methyl-N'-[4-(4-trifluoromethoxybenzyloxy)phenyl]-piperidine-1-carboxamidine Salt: TFA×2
Mass: ES+ 465.3

Example 114

N-(3-Aminopropyl)-4-methyl-N'-[4-(4-trifluoromethoxybenzyloxy)phenyl]-piperidine-1-carboxamidine Salt: TFA×2
Mass: ES+ 465.3

Example 115

N-(3-Aminopropyl)-2-methyl-N'-[4-(4-trifluoromethoxybenzyloxy)phenyl]-piperidine-1-carboxamidine Salt: TFA×2
Mass: ES+ 465.3

Example 116

N-(3-Aminopropyl)-2-ethyl-N'-[4-(4-trifluoromethoxybenzyloxy)phenyl]-piperidine-1-carboxamidine Salt: TFA×2
Mass: ES+ 479.3

Example 117

N'-(3-Aminopropyl)-N-ethyl-N-isopropyl-N''-[4-(4-trifluoromethoxybenzyloxy)-phenyl]guanidine Salt: TFA×2
Mass: ES+ 453.3

Example 118

N-(3-Amino-2,2-dimethylpropyl)-4-benzyl-N'-[4-(4-methylbenzyloxy)phenyl]-piperidine-1-carboxamidine Salt: TFA×2
Mass: ES+ 499.3

Example 119

N-(3-Amino-2,2-dimethylpropyl)-3-methyl-N'-[4-(4-methylbenzyloxy)phenyl]-piperidine-1-carboxamidine Salt: TFA×2
Mass: ES+ 423.3

Example 120

N-(3-Amino-2,2-dimethylpropyl)-4-methyl-N'-[4-(4-methylbenzyloxy)phenyl]-piperidine-1-carboxamidine Salt: TFA×2
Mass: ES+ 423.3

Example 121

N-(3-Amino-2,2-dimethylpropyl)-2-methyl-N'-[4-(4-methylbenzyloxy)phenyl]-piperidine-1-carboxamidine Salt: TFA×2
Mass: ES+ 423.3

Example 122

N-(3-Amino-2,2-dimethylpropyl)-2-ethyl-N'-[4-(4-methylbenzyloxy)phenyl]-piperidine-1-carboxamidine Salt: TFA×2
Mass: ES+ 437,3

Example 123

N'-(3-Amino-2,2-dimethylpropyl)-N-ethyl-N-isopropyl-N"-[4-(4-methylbenzyloxy)phenyl]guanidine Salt: TFA×2
Mass: ES+ 411.3

Example 124

N-(3-Amino-2,2-dimethylpropyl)-N'-[4-(2-methoxyethoxy)phenyl]-3-methylpiperidine-1-carboxamidine Salt: TFA×2
Mass: ES+ 377.3

Example 125

N-(3-Amino-2,2-dimethylpropyl)-N'-[4-(2-methoxyethoxy)phenyl]-4-methylpiperidine-1-carboxamidine Salt: TFA×2
Mass: ES+ 377.3

Example 126

N-(3-Amino-2,2-dimethylpropyl)-N'-[4-(2-methoxyethoxy)phenyl]-2-methylpiperidine-1-carboxamidine Salt: TFA×2
Mass: ES+ 377.3

Example 127

N-(3-Amino-2,2-dimethylpropyl)-2-methyl-N'-[4-(3-methylbut-2-enyloxy)-phenyl]piperidine-1-carboxamidine Salt: TFA×2
Mass: ES+ 387.3

Example 128

N-(3-Amino-2,2-dimethylpropyl)-3-methyl-N'-[4-(3-methylbutoxy)phenyl]-piperidine-1-carboxamidine Salt: TFA×2
Mass: ES+ 389.4

Example 129

N-(3-Amino-2,2-dimethylpropyl)-4-methyl-N'-[4-(3-methylbutoxy)phenyl]-piperidine-1-carboxamidine Salt: TFA×2
Mass: ES+ 389.4

Example 130

N-(3-Amino-2,2-dimethylpropyl)-2-methyl-N'-[4-(3-methylbutoxy)phenyl]-piperidine-1-carboxamidine Salt: TFA×2
Mass: ES+ 389.4

Example 131

N-(3-Amino-2,2-dimethylpropyl)-2-ethyl-N'-[4-(3-methylbutoxy)phenyl]-piperidine-1-carboxamidine Salt: TFA×2
Mass: ES+ 403.4

Example 132

N'-(3-Amino-2,2-dimethylpropyl)-N-ethyl-N-isopropyl-N"-[4-(3-methylbutoxy)-phenyl]guanidine Salt: TFA×2
Mass: ES+ 377.4

Example 133

N-(3-Amino-2,2-dimethylpropyl)-N'-(4-decyloxyphenyl)-3-methylpiperidine-1-carboxamidine Salt: TFA×2
Mass: ES+ 459.4

Example 134

N-(3-Amino-2,2-dimethylpropyl)-N'-(4-decyloxyphenyl)-4-methylpiperidine-1-carboxamidine Salt: TFA×2
Mass: ES+ 459.5

Example 135

N-(3-Amino-2,2-dimethylpropyl)-N'-(4-decyloxyphenyl)-2-methylpiperidine-1-carboxamidine Salt: TFA×2
Mass: ES+ 459.5

Example 136

N-(3-Amino-2,2-dimethylpropyl)-N'-(4-decyloxyphenyl)-2-ethylpiperidine-1-carboxamidine Salt: TFA×2
Mass: ES+ 473.5

Example 137

N'-(3-Amino-2,2-dimethylpropyl)-N''-(4-decyloxyphenyl)-N-ethyl-N-isopropyl-guanidine Salt: TFA×2
Mass: ES+ 447.5

Example 138

N-(3-Amino-22-dimethylpropyl)-4-benzy-N'-(4-propoxyphenyl)piperidine-1-carboxamidine Salt: TFA×2
Mass: ES+ 437.4

Example 139

N-(3-Amino-2,2-dimethylpropyl)-3-methyl-N'-(4-propoxyphenyl)piperidine-1-carboxamidine Salt: TFA×2
Mass: ES+ 361.4

Example 140

N-(3-Amino-2,2-dimethylpropyl)-4-methyl-N'-(4-propoxyphenyl)piperidine-1-carboxamidine Salt: TFA×2
Mass: ES+ 361.4

Example 141

N-(3-Amino-2,2-dimethylpropyl)-2-methyl-N'-(4-propoxyphenyl)piperidine-1-carboxamidine Salt: TFA×2
Mass: ES+ 361.4

Example 142

N-(3-Amino-2,2-dimethylpropyl)-2-ethyl-N'-(4-propoxyphenyl)piperidine-1-carboxamidine Salt: TFA×2
Mass: ES+ 375.4

Example 143

N'-(3-Amino-2,2-dimethylpropyl)-N-ethyl-N-isopropyl-N''-(4-propoxyphenyl)-guanidine Salt: TFA×2
Mass: ES+ 349.4

Example 144

N-(3-Amino-2,2-dimethylpropyl)-4-benzyl-N'-[4-(5-methylhexyloxy)phenyl]-piperidine-1-carboxamidine Salt: TFA×2
Mass: ES+ 493.5

Example 145

N-(3-Amino-2,2-dimethylpropyl)-3-methyl-N'-[4-(5-methylhexyloxy)phenyl]-piperidine-1-carboxamidine Salt: TFA×2
Mass: ES+ 417.4

Example 146

N-(3-Amino-2,2-dimethylpropyl)-4-methyl-N'-[4-(5-methylhexyloxy)phenyl]-piperidine-1-carboxamidine Salt: TFA×2
Mass: ES+ 417.4

Example 147

N-(3-Amino-2,2-dimethylpropyl)-2-methyl-N'-[4-(5-methylhexyloxy)phenyl]-piperidine-1-carboxamidine Salt: TFA×2
Mass: ES+ 417.4

Example 148

N-(3-Amino-2,2-dimethylpropyl)-2-ethyl-N'-[4-(5-methylhexyloxy)phenyl]-piperidine-1-carboxamidine Salt: TFA×2
Mass: ES+ 431.4

Example 149

N'-(3-Amino-2,2-dimethylpropyl)-N-ethyl-N-isopropyl-N''-[4-(5-methylhexyloxy)phenyl]guanidine Salt: TFA×2
Mass: ES+ 405.4

Example 150

N-(3-Amino-2,2-dimethylpropyl)-N'-[4-(4-tert-butylbenzyloxy)phenyl]-3-methylpiperidine-1-carboxamidine Salt TFA×2
Mass: ES+ 465.4

Example 151

N-(3-Amino-2,2-dimethylpropyl)-N'-[4-(4-tert-butyl-benzyloxy)phenyl]-4-methylpiperidine-1-carboxamidine Salt: TFA×2
Mass: ES+ 465.4

Example 152

N-(3-Amino-2,2-dimethylpropyl)-N'-[4-(4-tert-butyl-benzyloxy)phenyl]-2-methylpiperidine-1-carboxamidine Salt: TFA×2
Mass: ES+ 465.4

Example 153

N-(3-Amino-2,2-dimethylpropyl)-N'-[4-(4-tert-butyl-benzyloxy)phenyl]-2-ethyl-piperidine-1-carboxamidine Salt: TFA×2
Mass: ES+ 479.4

Example 154

N'-(3-Amino-2,2-dimethylpropyl)-N''-[4-(4-tert-butylbenzyloxy)phenyl]-N-ethyl-N-isopropylguanidine Salt: TFA×2
Mass: ES+ 453.4

Example 155

N-(3-Amino-2,2-dimethylpropyl)-4-benzyl-N'-[4-(4-cyanobenzyloxy)phenyl]-piperidine-1-carboxamidine Salt: TFA×2
Mass: ES+ 510.4

Example 156

N-(3-Amino-2,2-dimethylpropyl)-N'-[4-(4-cyanobenzyloxy)phenyl]-3-methylpiperidine-1-carboxamidine Salt: TFA×2
Mass: ES+ 434.4

Example 157

N-(3-Amino-2,2-dimethylpropyl)-N'-[4-(4-cyanobenzyloxy)phenyl]-4-methylpiperidine-1-carboxamidine Salt: TFA×2
Mass: ES+ 434.4

Example 158

N-(3-Amino-2,2-dimethylpropyl)-N'-[4-(4-cyanobenzyloxy)phenyl]-2-methylpiperidine-1-carboxamidine Salt: TFA×2
Mass: ES+ 434.4

Example 159

N'-(3-Amino-2,2-dimethylpropyl)-N''-[4-(4-cyanobenzyloxy)phenyl]-N-ethyl-N-isopropylguanidine Salt: TFA×2
Mass: ES+ 422.4

Example 160

N-(3-Amino-2,2-dimethylpropyl)-N'-[4-(2-cyanobenzyloxy)phenyl]-3-methylpiperidine-1-carboxamidine Salt: TFA×2
Mass: ES+ 434.4

Example 161

N-(3-Amino-2,2-dimethylpropyl)-N'-[4-(2-cyanobenzyloxy)phenyl]-2-methylpiperidine-1-carboxamidine Salt: TFA×2
Mass: ES+ 434.4

Example 162

N'-(3-Amino-2,2-dimethylpropyl)-N''-[4-(2-cyanobenzyloxy)phenyl]-N-ethyl-N-isopropylguanidine Salt: TFA×2
Mass: ES+ 422.4

Example 163

N-(3-Amino-2,2-dimethylpropyl)-4-benzyl-N'-[4-(2-cyclohexylethoxy)phenyl]-piperidine-1-carboxamidine Salt: TFA×2
Mass: ES+ 505.4

Example 164

N-(3-Amino-2,2-dimethylpropyl)-N'-[4-(2-cyclohexylethoxy)phenyl]-3-methylpiperidine-1-carboxamidine Salt: TFA×2
Mass: ES+ 429.4

Example 165

N-(3-Amino-2,2-dimethylpropyl)-N'-[4-(2-cyclohexylethoxy)phenyl]-4-methylpiperidine-1-carboxamidine Salt: TFA×2
Mass: ES+ 429.4

Example 166

N-(3-Amino-2,2-dimethylpropyl)-N'-[4-(2-cyclohexylethoxy)phenyl]-2-methylpiperidine-1-carboxamidine Salt: TFA×2
Mass: ES+ 429.4

Example 167

N-(3-Amino-2,2-dimethylpropyl)-N'-[4-(2-cyclohexylethoxy)phenyl]-2-ethylpiperidine-1-carboxamidine Salt: TFA×2
Mass: ES+ 443.5

Example 168

N'-(3-Amino-2,2-dimethylpropyl)-N''-[4-(2-cyclohexylethoxy)phenyl]-N-ethyl-N-isopropylguanidine Salt: TFA×2
Mass: ES+ 417.4

Example 169

N-(3-Amino-2,2-dimethylpropyl)-4-benzyl-N'-[4-(3-cyanopropoxy)phenyl]-piperidine-1-carboxamidine Salt: TFA×2
Mass: ES+ 462.4

Example 170

N-(3-Amino-2,2-dimethylpropyl)-N'-[4-(3-cyanopropoxy)phenyl]-3-methyl-piperidine-1-carboxamidine Salt: TFA×2
Mass: ES+ 386.4

Example 171

N-(3-Amino-2,2-dimethylpropyl)-N'-[4-(3-cyanopropoxy)phenyl]-4-methylpiperidine-1-carboxamidine Salt: TFA×2
Mass: ES+ 386.4

Example 172

N-(3-Amino-2,2-dimethylpropyl)-N'-[4-(3-cyanopropoxy)phenyl]-2-ethylpiperidine-1-carboxamidine Salt: TFA×2
Mass: ES+ 400.4

Example 173

N-(3-Amino-2,2-dimethylpropyl)-4-benzyl-N'-[4-(2-methylbenzyloxy)phenyl]-piperidine-1-carboxamidine Salt: TFA×2
Mass: ES+ 499.4

Example 174

N-(3-Amino-2,2-dimethylpropyl)-3-methyl-N'-[4-(2-methylbenzyloxy)phenyl]-piperidine-1-carboxamidine Salt: TFA×2
Mass: ES+ 423.4

Example 175

N-(3-Amino-2,2-dimethylpropyl)-2-methyl-N'-[4-(2-methylbenzyloxy)phenyl]-piperidine-1-carboxamidine Salt: TFA×2
Mass: ES+ 423.4

Example 176

N-(3-Amino-2,2-dimethylpropyl)-2-ethyl-N'-[4-(2-methylbenzyloxy)phenyl]-piperidine-1-carboxamidine Salt: TFA×2
Mass: ES+ 437.4

Example 177

N'-(3-Amino-2,2-dimethylpropyl)-N-ethyl-N-isopropyl-N''-[4-(2-methylbenzyloxy)phenyl]guanidine Salt: TFA×2
Mass: ES+ 411.4

Example 178

N-(3-Amino-2,2-dimethylpropyl)-4-benzyl-N'-[4-(3-trifluoromethoxybenzyloxy)phenyl]piperidine-1-carboxamidine Salt: TFA×2
Mass: ES+ 569.3

Example 179

N-(3-Amino-2,2-dimethylpropyl)-3-methyl-N'-[4-(3-trifluoromethoxybenzyloxy)phenyl]piperidine-1-carboxamidine Salt: TFA×2
Mass: ES+ 493.3

Example 180

N-(3-Amino-2,2-dimethylpropyl)-2-methyl-N'-[4-(3-trifluoromethoxybenzyl-oxy)phenyl]piperidine-1-carboxamidine Salt: TFA×2
Mass: ES+ 493.3

Example 181

N-(3-Amino-2,2-dimethylpropyl)-2-ethyl-N'-[4-(3-trifluoromethoxybenzyloxy)-phenyl]piperidine-1-carboxamidine Salt: TFA×2
Mass: ES+ 507.3

Example 182

N-(3-Amino-2,2-dimethylpropyl)-4-benzyl-N'-[4-(4,4,4-trifluorobutoxy)phenyl]-piperidine-1-carboxamidine Salt: TFA×2
Mass: ES+ 505.4

Example 183

N-(3-Amino-2,2-dimethylpropyl)-4-methyl-N'-[4-(4,4,4-trifluorobutoxy)phenyl]-piperidine-1-carboxamidine Salt: TFA×2
Mass: ES+ 429.3

Example 184

N-(3-Amino-2,2-dimethylpropyl)-2-ethyl-N'-[4-(4,4,4-trifluorobutoxy)phenyl]-piperidine-1-carboxamidine Salt: TFA×2
Mass: ES+ 443.4

Example 185

N-(3-Amino-2,2-dimethylpropyl)-4-benzyl-N'-(4-pentyloxyphenyl)piperidine-1-carboxamidine Salt: TFA×2
Mass: ES+ 465.4

Example 186

N-(3-Amino-2,2-dimethylpropyl)-2-methyl-N'-(4-pentyloxyphenyl)piperidine-1-carboxamidine Salt: TFA×2
Mass: ES+ 399.4

Example 187

N-(3-Amino-2,2-dimethylpropyl)-2-ethyl-N'-(4-pentyloxyphenyl)piperidine-1-carboxamidine Salt: TFA×2
Mass: ES+ 403.4

Example 188

N-(3-Amino-2,2-dimethylpropyl)-4-benzyl-N'-[4-(4-methanesulfonylbenzyloxy)phenyl]piperidine-1-carboxamidine Salt: TFA×2
Mass: ES+ 563.4

Example 189

N-(3-Amino-2,2-dimethylpropyl)-N'-[4-(4-methanesulfonylbenzyloxy)phenyl]-3-methylpiperidine-1-carboxamidine Salt: TFA×2
Mass: ES+ 487.3

Example 190

N-(3-Amino-2,2-dimethylpropyl)-N'-[4-(4-methanesulfonylbenzyloxy)phenyl]-4-methylpiperidine-1-carboxamidine Salt: TFA×2
Mass: ES+ 487.3

Example 191

N-(3-Amino-2,2-dimethylpropyl)-N'-[4-(4-methanesulfonylbenzyloxy)phenyl]-2-methylpiperidine-1-carboxamidine Salt: TFA×2
Mass: ES+ 487.3

Example 192

N-(3-Amino-2,2-dimethylpropyl)-2-ethyl-N'-[4-(4-methanesulfonylbenzyloxy)-phenyl]piperidine-1-carboxamidine Salt: TFA×2
Mass: ES+ 501.3

Example 193

N'-(3-Amino-2,2-dimethylpropyl)-N-ethyl-N-isopropyl-N''-[4-(4-methanesulfonylbenzyloxy)phenyl]guanidine Salt: TFA×2
Mass: ES+ 475.3

Example 194

N-(3-Amino-2,2-dimethylpropyl)-4-benzyl-N'-[4-(4-trifluoromethoxybenzyloxy)phenyl]piperidine-1-carboxamidine Salt: TFA×2
Mass: ES+ 569.4

Example 195

N-(3-Amino-2,2-dimethylpropyl)-4-methyl-N'-[4-(4-trifluoromethoxybenzyloxy)phenyl]piperidine-1-carboxamidine Salt: TFA×2
Mass: ES+ 493.3

Example 196

N-(3-Amino-2,2-dimethylpropyl)-2-methyl-N'-[4-(4-trifluoromethoxybenzyloxy)phenyl]piperidine-1-carboxamidine Salt: TFA×2
Mass: ES+ 493.3

Example 197

N-(3-Amino-2,2-dimethylpropyl)-2-ethyl-N'-[4-(4-trifluoromethoxybenzyloxy)-phenyl]piperidine-1-carboxamidine Salt: TFA×2
Mass: ES+ 507.4

Example 198

N'-(3-Amino-2,2-dimethylpropyl)-N-ethyl-N-isopropyl-N''-[4-(4-trifluoromethoxybenzyloxy)phenyl]guanidine Salt: TFA×2
Mass: ES+ 481.3

RESULTS

The activity of the compounds of the present invention is demonstrated in vitro in the following tests:

The stably transfected cell line (luciferase under the control of the human CETP promoter) is maintained in the growth medium (DMEM/Hepes, F12, Glutamax, FBS and geneticin) incubated at 37° C., 95% humidity and 5% $CO_2$ to the point of confluence. The cells are then rinsed with PBS and detached with a trypsin/EDTA mixture. The medium is changed every 2 to 3 days.

The resuspended cells are diluted and counted, and then distributed in microplate (96) wells.

About 20 000 cells per well are distributed and incubated overnight at 37° C. with 5% $CO_2$.

The compounds of the present invention are diluted to a final concentration of 15 µM and distributed in the plates containing the cells.

The plates are incubated overnight at 37° C. with 5% $CO_2$.

The medium covering the cells is drawn off and 100 µl of Steady Glo luciferase (DMEM without phenol red/Steady Glo, V/V) are added to the cells.

The plates are sealed with a film and left in the dark for about 20 minutes at room temperature.

The plates are then read using a luminometer (1 sec/well).

The inhibition of CETP expression by the products is expressed as a percentage of the control:

$$\% \ CTRL = \frac{\text{mean product } CPS}{\text{mean control } CPS} \times 100$$

By way of example, the activity expressed as a percentage of the control for the compounds of Examples 5, 31, 61 and 95 is 46%, 30%, 33% and 16%, respectively.

On another batch of plates not treated with Steady Glo, the state of the cultures is checked by microscope. The culture medium is removed and 100 µl of medium comprising neutral red are added for 3 hours at 37° C.

The medium is then removed and replaced for one minute with 100 µl of formaldehyde-calcium (10 ml of 37% formaldehyde+calcium chloride dihydrate 10 g qs 1 L).

The plate is emptied and 100 µl of acetic acid-ethanol mixture (10 ml of glacial acetic acid+500 ml of absolute ethanol qs 1 L) are added to each well for 15 minutes with stirring.

The plates are then read at 540 nm. The stronger the coloration, the greater the cellular toxicity.

No cellular toxicity is detected for the compounds of Examples 5, 31, 61 and 95.

The invention claimed is:

1. A compound of formula (I):

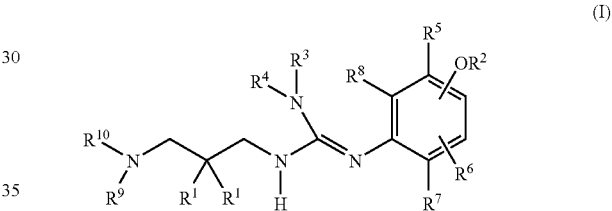

wherein:
$R^1$ is in each case hydrogen, or $(C_1-C_6)$alkyl, or alternatively the two radicals $R^1$ form, together with the carbon atom that bears them, $(C_3-C_{10})$cycloalkyl;
$R^2$ is $(C_1-C_{10})$alkyl, $(C_2-C_{10})$alkenyl, $(C_6-C_{18})$aryl$(C_1-C_{10})$alkyl, $(C_1-C_6)$alkyl-O—$(C_1-C_{10})$alkyl, or $(C_3-C_{10})$cycloalkyl$(C_1-C_{10})$alkyl;
$R^3$ and $R^4$, which may be identical or different, are each, independently, hydrogen, $(C_1-C_{10})$alkyl, $(C_2-C_{10})$alkenyl, $(C_6-C_{18})$aryl$(C_1-C_{10})$alkyl, $(C_1-C_6)$alkyl-O—$(C_1-C_{10})$alkyl, or $(C_3-C_{10})$cycloalkyl$(C_1-C_{10})$alkyl, or alternatively
$R^3$ and $R^4$ form, together with the nitrogen atom that bears them, a 3- to 9-membered heterocycle;
$R^5$, $R^6$, $R^7$ and $R^8$, which may be identical or different, are each, independently, hydrogen, $(C_1-C_{10})$alkyl, a $(C_1-C_{10})$alkenyl, $(C_1-C_6)$alkyl-O—; and
$R^9$ is hydrogen, and $R^{10}$ is hydrogen or $(C_1-C_6)$alkyl, or alternatively
$R^9$ and $R^{10}$ form, together with the nitrogen atom that bears them, a 3- to 7-membered heterocycle;
wherein alkyl, aryl, and heterocyclic groups listed above are in each case unsubstituted or substituted one or more times by G;
G is trifluoromethyl, styryl, halogen, Het which is unsubstituted or substituted one or more times by T, Het-CO— which is unsubstituted substituted one or more times by T, nitro, cyano, $(C_1-C_{10})$alkyl, $(C_1-C_{10})$alkylcarbonyl, $(C_1-C_{10})$alkoxycarbonyl-A-, $(C_3-C_{10})$cycloalkyl, trifluoromethoxy, di$(C_1-C_{10})$alkylamino, $(C_1-C_{10})$alkoxy$(C_1-C_{10})$alkyl, $(C_1-C_{10})$alkoxy, $(C_6-C_{18})$aryl which is unsubstituted or substituted one or more times by T, $(C_6-C_{18})$aryl$(C_1-C_{10})$alkoxy-$(CO)_n$— which is unsubstituted or substituted one or more times by T, $(C_6-C_{18})$aryloxy $(CO)_n$— which is unsubstituted or substituted one or more times by T, $(C_6-C_{18})$arylthio in which aryl is unsubstituted or substituted one or more times by T, $(C_6-C_{18})$aryloxy-$(C_1-C_{10})$alkyl$(CO)_n$— in which aryl is unsubstituted or substituted one or more times by T, monocyclic 5- to 8-membered heterocycle containing one or more hetero atoms chosen from O, N and S and which is unsubstituted or substituted one or more times by T, $(C_6-C_{18})$aryl-carbonyl which is unsubstituted or substituted one or more times by T, $(C_6-C_{18})$arylcarbonyl-B—$(CO)_n$—, $(C_6-C_{18})$aryl-C'—$(CO)_n$— wherein aryl is unsubstituted or substituted one or more times by T, $(C_6-C_{18})$aryl which is fused to a saturated or unsaturated heterocycle and which is unsubstituted or substituted one or more times by T, or $(C_2-C_{10})$alkynyl;

T is halogen, $(C_6-C_{18})$aryl, $(C_1-C_6)$alkyl, $(C_1-C_6)$alkoxy, $(C_1-C_6)$alkoxy-$(C_6-C_{18})$aryl, nitro, carboxyl, $(C_1-C_6)$alkoxycarboxyl, $(C_1-C_6)$alkoxy-carbonyl $(C_1-C_6)$alkyl, or $(C_1-C_6)$alkylcarbonyl$((C_1-C_6)$alkyl$)_n$—, or T can also be oxo in the case where it substitutes a saturated or unsaturated heterocycle, or if two vicinal carbon atoms are substituted, T can also be a $C_1-C_6$ alkylenediyl chain or a $C_1-C_6$ alkylenedioxy chain;

Het is a monocyclic, bicyclic or tricyclic aromatic heterocyclic radical containing one or more hetero atoms chosen from O, N and S;

A is $(C_1-C_6)$alkylene, $(C_2-C_6)$alkenylene or a bond;

n is 0 or 1;

B represents $(C_1-C_6)$alkylene or $(C_2-C_6)$alkenylene and aryl is optionally substituted by one or more radicals T; and C' represents $(C_1-C_6)$alkylene or $(C_2-C_6)$alkenylene;

or an optical or geometrical isomer thereof, an oxide form thereof, a tautomeric form thereof; or a pharmaceutically acceptable addition salt thereof.

2. A compound according to claim 1, wherein in which alkyl groups are in each case unsubstituted or ω-monosubstituted.

3. A compound according to claim 1, wherein $R^8$ is hydrogen.

4. A compound according to claim 1, wherein $R^7$ is hydrogen.

5. A compound according to claim 1, wherein $R^6$ is hydrogen.

6. A compound according to claim 1, wherein $R^5$ is hydrogen.

7. A compound according to claim 1, wherein $R^1$ is hydrogen or $(C_1-C_6)$alkyl.

8. A compound according to claim 1, wherein $R^2$ is unsubstituted $(C_1-C_{10})$alkyl, ω-monosubstituted $(C_1-C_{10})$alkyl, $(C_2-C_{10})$alkenyl, $(C_6-C_{18})$aryl-$(C_1-C_{10})$alkyl wherein the aryl portion is unsubstituted or monosubstituted, $(C_1-C_6)$alkyl-O—$(C_1-C_{10})$alkyl, or $(C_3-C_{10})$cycloalkyl$(C_1-C_{10})$alkyl.

9. A compound according to claim 1, wherein $R^9$ and $R^{10}$ are each hydrogen.

10. A compound according to claim 1, wherein $R^3$ and $R^4$ are each $(C_1-C_6)$alkyl, or alternatively $R^3$ is hydrogen atom and $R^4$ is $(C_1-C_{10})$alkyl, or alternatively $R^3$ and $R^4$ form, together with the nitrogen atom that bears them, a 5- or 6-membered heterocycle.

11. A compound according to claim 1, wherein:
$R^1$ hydrogen or methyl;
$R^2$ is unsubstituted $(C_1-C_{10})$alkyl, ω-mono-substituted $(C_1-C_{10})$alkyl, $(C_2-C_{10})$alkenyl, phenyl$(C_1-C_{10})$alkyl wherein the aryl portion is unsubstituted or monosubstituted, $(C_1-C_6)$-alkyl-O—$(C_1-C_{10})$alkyl, or $(C_3-C_6)$cycloalkyl$(C_1-C_{10})$alkyl;
$R^3$ and $R^4$ are each $(C_1-C_6)$alkyl, or alternatively $R^3$ is hydrogen and $R^4$ is $(C_1-C_{10})$alkyl, or alternatively $R^3$ and $R^4$ form, together with the nitrogen atom that bears them, a 5- or 6-membered heterocycle;
$R^5$ hydrogen;
$R^6$ is hydrogen;
$R^7$ hydrogen;
$R^8$ is hydrogen; and/or
$R^9$ and $R^{10}$ are each hydrogen.

12. A compound according to claim 1, wherein:
$R^1$ hydrogen or methyl;
$R^2$ is unsubstituted $(C_1-C_{10})$alkyl, ω-mono-substituted $(C_1-C_{10})$alkyl, $(C_2-C_{10})$alkenyl radical, phenyl$(C_1-C_{10})$alkyl wherein the aryl portion is unsubstituted or monosubstituted, $(C_1-C_6)$alkyl-O—$(C_1-C_{10})$alkyl, or $(C_3-C_6)$cycloalkyl$(C_1-C_{10})$alkyl;
$R^3$ and $R^4$ are each $(C_1-C_6)$alkyl, or alternatively $R^3$ is hydrogen and $R^4$ is $(C_1-C_{10})$alkyl, or alternatively $R^3$ and $R^4$ form, together with the nitrogen atom that bears them, a 5- or 6-membered heterocycle;
$R^5$, $R^6$, $R^7$ and $R^8$ are each hydrogen; and
$R^9$ $R^{10}$ are each hydrogen.

13. A compound according to claim 1, wherein said compound is selected from:

N-(3-Amino-2,2-dimethylpropyl)-N'-(4-benzyloxyphenyl)-N''-(3-methylbutyl)guanidine;

N-(3-Aminopropyl)-2-methyl-N'-[4-(2-methylbenzyloxy)phenyl]piperidine-1-carboxamidine;

N-(3-Aminopropyl)-N'-(3-methylbutyl)-N''-(4-pentyloxyphenyl)guanidine;

N-(3-Aminopropyl)-N'-[4-(2-methoxyethoxy)phenyl]-3-methylpiperidine-1-carboxamidine;

N-(3-Aminopropyl)-N'-[4-(2-methoxyethoxy)phenyl]-4-methylpiperidine-1-carboxamidine;

N'-(3-Aminopropyl)-N-ethyl-N-isopropyl-N''-[4-(2-methoxyethoxy)phenyl]guanidine;

N-(3-Aminopropyl)-4-methyl-N'-[4-(3-methylbutoxy)phenyl]piperidine-1-carboxamidine;

N-(3-Aminopropyl)-2-methyl-N'-[4-(3-methylbutoxy)phenyl]piperidine-1-carboxamidine;

N-(3-Aminopropyl)-2-ethyl-N'-[4-(3-methylbutoxy)phenyl]piperidine-1-carboxamidine;

N'-(3-Aminopropyl)-N-ethyl-N-isopropyl-N''-[4-(3-methylbutoxy)phenyl]guanidine;

N-(3-Aminopropyl)-3-methyl-N'-(4-propoxyphenyl)piperidine-1-carboxamidine;

N-(3-Aminopropyl)-4-methyl-N'-(4-propoxyphenyl)piperidine-1-carboxamidine;

N-(3-Aminopropyl)-2-methyl-N'-(4-propoxyphenyl)piperidine-1-carboxamidine;

N-(3-Aminopropyl)-2-ethyl-N'-(4-propoxyphenyl)piperidine-1-carboxamidine;

N'-(3-Aminopropyl)-N-ethyl-N-isopropyl-N''-(4-propoxyphenyl)guanidine;

N-(3-Aminopropyl)-N'-[4-(4-tert-butylbenzyloxy)phenyl]-2-methylpiperidine-1-carboxamidine;

N-(3-Aminopropyl)-N'-[4-(4-tert-butylbenzyloxy)phenyl]-2-ethylpiperidine-1-carboxamidine;
N-(3-Aminopropyl)-4-benzyl-N'-[4-(4,4,4-trifluorobutoxy)phenyl]piperidine-1-carboxamidine;
N-(3-Aminopropyl)-2-ethyl-N'-(4-pentyloxyphenyl)piperidine-1-carboxamidine;
N'-(3-Amino-2,2-dimethylpropyl)-N-ethyl-N-isopropyl-N''-[4-(2-methylbenzyl-oxy)phenyl]guanidine; and
optical and geometrical isomers, oxide forms and tautomeric forms thereof, and also the pharmaceutically acceptable addition salts thereof.

14. A process for the preparation of a compound according to claim 1, said process comprises: reacting an aryl thiocyanate (V)

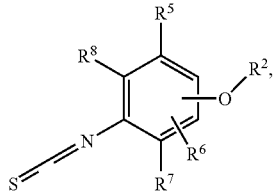
(V)

with an amine $HNR^3R^4$, in a polar protic medium, to give, after heating, the corresponding thiourea,
placing said thiourea in a reducing medium with an amine of formula (III)

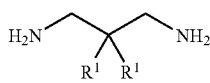
(III)

to give a compound of formula (I), and
optionally isolating and purifying said compound of formula (I).

15. A process according to claim 14, wherein $R^5$, $R^6$, $R^7$ and $R^8$ are each hydrogen.

16. A process for the preparation of a compound according to claim 1, said process comprises:
contacting a compound of formula (II):

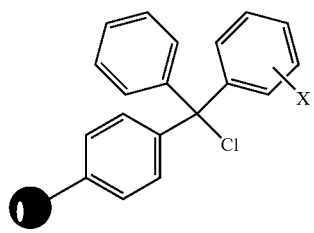
(II)

wherein

represents a graft on resin; and
X is hydrogen, halogen, $(C_1-C_6)$alkyl, or $(C_1-C_6)$alkoxy;
with an excess of an amine of formula (III)

(III)

in an apolar aprotic solvent to give a compound of formula (IV)

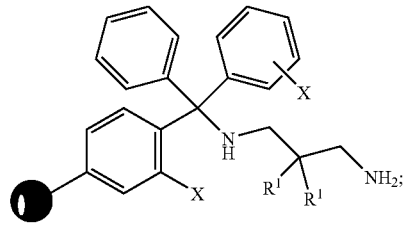
(IV)

reacting said compound of formula (IV) with a compound of the formula (V)

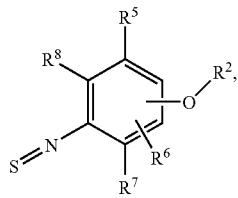
(V)

to give a thiourea of formula (VI)

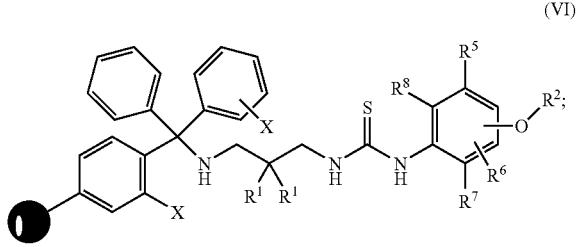
(VI)

converting said thiourea of formula (VI) by the action of an amine of formula (VII)

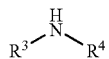
(VII)

in a polar aprotic medium, and in the presence of a mercuric salt to give the guanidine of formula (VIII)

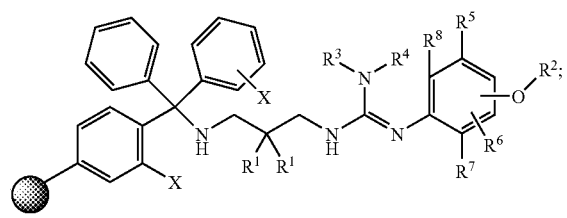
(VIII)

detaching said guanidine of formula (VIII) from the resin, to give a compound of formula (I) wherein $R^9$ and $R^{10}$ are each hydrogen; and
optionally selectively monoalkylating the terminal amine of said compound of formula (I).

17. A process according to claim 16, wherein $R^4$, $R^5$, $R^6$, $R^7$ and $R^8$ are each hydrogen, $R^3$ is alkyl and $R^2$ is benzyl.

18. A pharmaceutical composition comprising a pharmaceutically effective amount of at least one compound according to claim 1, in combination with one or more pharmaceutically acceptable vehicles.

19. A method for treating a patient suffering from dyslipidaemia, atherosclerosis or type II diabetes, comprising administering to said patient a compound according to claim 1.

20. A compound according to claim 1, wherein

G is trifluoromethyl, halogen, amino, nitro, cyano, ($C_1$-$C_{10}$)alkyl, ($C_2$-$C_6$)alkynyl, ($C_1$-$C_{10}$)alkylcarbonyl, ($C_3$-$C_{10}$)cycloalkyl, trifluoromethoxy, di($C_1$-$C_{10}$)alkylamino, ($C_1$-$C_{10}$)-alkoxy($C_1$-$C_{10}$)alkyl, ($C_1$-$C_{10}$)alkoxy, ($C_6$-$C_{18}$)aryl which is unsubstituted or one or more times by T, ($C_6$-$C_{18}$)aryloxy-$(CO)_{0-1}$— in which aryl is unsubstituted or substituted one or more times by T, ($C_6$-$C_{18}$)arylthio in which aryl is unsubstituted or substituted one or more times by T, or saturated or unsaturated, monocyclic 5- to 8-membered heterocycle comprising one or more hetero atoms selected from O, N and S, and which unsubstituted or substituted one or more times by T, or ($C_2$-$C_{10}$)alkynyl, and T is halogen, ($C_6$-$C_{18}$)aryl, ($C_1$-$C_6$)alkyl, ($C_1$-$C_6$)alkoxy, ($C_1$-$C_6$)alkoxy($C_6$-$C_{18}$)aryl, nitro, carboxyl, ($C_1$-$C_6$)alkoxycarboxyl, ($C_1$-$C_6$)alkoxycarbonyl($C_1$-$C_6$)alkyl, or ($C_1$-$C_6$)alkylcarbonyl(($C_1$-$C_6$)alkyl)$_n$—, or T can be oxo in the case where it substitutes a saturated or unsaturated heterocycle.

21. A compound according to claim 2, wherein

G is trifluoromethyl, halogen, amino, nitro, cyano, ($C_1$-$C_{10}$)alkyl, ($C_2$-$C_6$)alkynyl, ($C_1$-$C_{10}$)alkylcarbonyl, ($C_3$-$C_{10}$)cycloalkyl, trifluoromethoxy, di($C_1$-$C_{10}$)alkylamino, ($C_1$-$C_{10}$)-alkoxy($C_1$-$C_{10}$)alkyl, ($C_1$-$C_{10}$)alkoxy, ($C_6$-$C_{18}$)aryl which is unsubstituted or one or more times by T, ($C_6$-$C_{18}$)aryloxy-$(CO)_{0-1}$— in which aryl is unsubstituted or one or more times by T, ($C_6$-$C_{18}$)arylthio in which aryl is unsubstituted or one or more times by T, or saturated or unsaturated, monocyclic 5- to 8-membered heterocycle comprising one or more hetero atoms selected from O, N and S, and which unsubstituted or substituted one or more times by T, or ($C_2$-$C_{10}$)alkynyl, and T is halogen, ($C_6$-$C_{18}$)aryl, ($C_1$-$C_6$)alkyl, ($C_1$-$C_6$)alkoxy, ($C_1$-$C_6$)alkoxy($C_6$-$C_{18}$)aryl, nitro, carboxyl, ($C_1$-$C_6$)alkoxycarboxyl, ($C_1$-$C_6$)alkoxycarbonyl($C_1$-$C_6$)alkyl, or ($C_1$-$C_6$)alkylcarbonyl(($C_1$-$C_6$)alkyl)$_n$—, or T can be oxo in the case where it substitutes a saturated or unsaturated heterocycle.

22. A compound according to claim 11, wherein

G is trifluoromethyl, halogen, amino, nitro, cyano, ($C_1$-$C_{10}$)alkyl, ($C_2$-$C_6$)alkynyl, ($C_1$-$C_{10}$)alkylcarbonyl, ($C_3$-$C_{10}$)cycloalkyl, trifluoromethoxy, di($C_1$-$C_{10}$)alkylamino, ($C_1$-$C_{10}$)-alkoxy($C_1$-$C_{10}$)alkyl, ($C_1$-$C_{10}$)alkoxy, ($C_6$-$C_{18}$)aryl which is unsubstituted or one or more times by T, ($C_6$-$C_{18}$)aryloxy-$(CO)_{0-1}$— in which aryl is unsubstituted or one or more times by T, ($C_6$-$C_{18}$)arylthio in which aryl is unsubstituted or one or more times by T, or saturated or unsaturated, monocyclic 5- to 8-membered heterocycle comprising one or more hetero atoms selected from O, N and S, and which unsubstituted or substituted one or more times by T, or ($C_2$-$C_{10}$)alkynyl, and T is halogen, ($C_6$-$C_{18}$)aryl, ($C_1$-$C_6$)alkyl, ($C_1$-$C_6$)alkoxy, ($C_1$-$C_6$)alkoxy($C_6$-$C_{18}$)aryl, nitro, carboxyl, ($C_1$-$C_6$)alkoxycarboxyl, ($C_1$-$C_6$)alkoxycarbonyl($C_1$-$C_6$)alkyl, or ($C_1$-$C_6$)alkylcarbonyl(($C_1$-$C_6$)alkyl)$_n$—, or T can be oxo in the case where it substitutes a saturated or unsaturated heterocycle.

23. A compound according to claim 12, wherein

G is trifluoromethyl, halogen, amino, nitro, cyano, ($C_1$-$C_{10}$)alkyl, ($C_2$-$C_6$)alkynyl, ($C_1$-$C_{10}$)alkylcarbonyl, ($C_3$-$C_{10}$)cycloalkyl, trifluoromethoxy, di($C_1$-$C_{10}$)alkylamino, ($C_1$-$C_{10}$)-alkoxy($C_1$-$C_{10}$)alkyl, ($C_1$-$C_{10}$)alkoxy, ($C_6$-$C_{18}$)aryl which is unsubstituted or one or more times by T, ($C_6$-$C_{18}$)aryloxy-$(CO)_{0-1}$— in which aryl is unsubstituted or one or more times by T, ($C_6$-$C_{18}$)arylthio in which aryl is unsubstituted or one or more times by T, or saturated or unsaturated, monocyclic 5- to 8-membered heterocycle comprising one or more hetero atoms selected from O, N and S, and which unsubstituted or substituted one or more times by T, or ($C_2$-$C_{10}$)alkynyl, and T is halogen, ($C_6$-$C_{18}$)aryl, ($C_1$-$C_6$)alkyl, ($C_1$-$C_6$)alkoxy, ($C_1$-$C_6$)alkoxy($C_6$-$C_{18}$)aryl, nitro, carboxyl, ($C_1$-$C_6$)alkoxycarboxyl, ($C_1$-$C_6$)alkoxycarbonyl($C_1$-$C_6$)alkyl, or ($C_1$-$C_6$)alkylcarbonyl(($C_1$-$C_6$)alkyl)$_n$—, or T can be oxo in the case where it substitutes a saturated or unsaturated heterocycle.

24. A compound according to claim 1, wherein said compound is selected from:

N-(3-Amino-2,2-dimethylpropyl)-N'-(4-benzyloxyphenyl)-N''-(3-methylbutyl)guanidine bis(trifluoroacetate);

N-(3-Aminopropyl)-2-methyl-N'-[4-(2-methylbenzyloxy)phenyl]piperidine-1-carboxamidine bis(trifluoroacetate);

N-(3-Aminopropyl)-N'-(3-methylbutyl)-N''-(4-pentyloxyphenyl)guanidine bis(trifluoroacetate);

N-(3-Aminopropyl)-N'-[4-(2-methoxyethoxy)phenyl]-3-methylpiperidine-1-carboxamidine bis(trifluoroacetate);

N-(3-Aminopropyl)-N'-[4-(2-methoxyethoxy)phenyl]-4-methylpiperidine-1-carboxamidine bis(trifluoroacetate);

N'-(3-Aminopropyl)-N-ethyl-N-isopropyl-N''-[4-(2-methoxyethoxy)phenyl]guanidine bis(trifluoroacetate);

N-(3-Aminopropyl)-4-methyl-N'-[4-(3-methylbutoxy)phenyl]piperidine-1-carboxamidine bis(trifluoroacetate);

N-(3-Aminopropyl)-2-methyl-N'-[4-(3-methylbutoxy)phenyl]piperidine-1-carboxamidine bis(trifluoroacetate);

N-(3-Aminopropyl)-2-ethyl-N'-[4-(3-methylbutoxy)phenyl]piperidine-1-carboxamidine bis(trifluoroacetate);

N'-(3-Aminopropyl)-N-ethyl-N-isopropyl-N''-[4-(3-methylbutoxy)phenyl]guanidine bis(trifluoroacetate);

N-(3-Aminopropyl)-3-methyl-N'-(4-propoxyphenyl)piperidine-1-carboxamidine bis(trifluoroacetate);

N-(3-Aminopropyl)-4-methyl-N'-(4-propoxyphenyl)piperidine-1-carboxamidine bis(trifluoroacetate);

N-(3-Aminopropyl)-2-methyl-N'-(4-propoxyphenyl)piperidine-1-carboxamidine bis(trifluoroacetate);

N-(3-Aminopropyl)-2-ethyl-N'-(4-propoxyphenyl)piperidine-1-carboxamidine bis(trifluoroacetate);

N'-(3-Aminopropyl)-N-ethyl-N-isopropyl-N''-(4-propoxyphenyl)guanidine bis(trifluoroacetate);

N-(3-Aminopropyl)-N'-[4-(4-tert-butylbenzyloxy)phenyl]-2-methylpiperidine-1-carboxamidine bis(trifluoroacetate);

N-(3-Aminopropyl)-N'-[4-(4-tert-butylbenzyloxy)phenyl]-2-ethylpiperidine-1-carboxamidine bis(trifluoroacetate);

N-(3-Aminopropyl)-4-benzyl-N'-[4-(4,4,4-trifluorobutoxy)phenyl]piperidine-1-carboxamidine bis(trifluoroacetate);

N-(3-Aminopropyl)-2-ethyl-N'-(4-pentyloxyphenyl)piperidine-1-carboxamidine bis(trifluoroacetate); and N'-(3-Amino-2,2-dimethylpropyl)-N-ethyl-N-isopropyl-N''-[4-(2-methylbenzyl-oxy)phenyl]guanidine bis(trifluoroacetate).

25. A compound according to claim 1, wherein said compound is selected from:

N-(3-Amino-2,2-dimethylpropyl)-N'-(3-benzyloxyphenyl)-N''-(3-methylbutyl)guanidine;

N-(3-Amino-2,2-dimethylpropyl)-N'-(4-benzyloxyphenyl)-3-hydroxymethylpiperidine-1-carboxamidine;

N-(3-Amino-2,2-dimethylpropyl)-N'-(4-benzyloxyphenyl)pyrrolidine-1-carboxamidine;

N-(3-Aminopropyl)-N'-(3-benzyloxyphenyl)pyrrolidine-1-carboxamidine; N-(3-Aminopropyl)-N'-(4-benzyloxyphenyl)-N''-phenethylguanidine;

N-(3-Aminopropyl)-N'-(3-benzyloxyphenyl)-N''-(3-methylbutyl)guanidine;

N-(3-Aminopropyl)-N'-(3-benzyloxyphenyl)-3-hydroxymethylpiperidine-1-carboxamidine;

N-(3-Aminopropyl)-N'-(4-benzyloxyphenyl)pyrrolidine-1-carboxamidine;

N-(3-Aminopropyl)-N'-(4-benzyloxyphenyl)-3-hydroxymethylpiperidine-1-carboxamidine;

N-(3-Aminopropyl)-N'-(4-benzyloxyphenyl)-N''-(3-methylbutyl)guanidine;

N-(3-Amino-2,2-dimethylpropyl)-N'-(3-benzyloxyphenyl)-3-hydroxymethylpiperidine-1-carboxamidine;

N-(3-Amino-2,2-dimethylpropyl)-N'-(3-benzyloxyphenyl)pyrrolidine-1-carboxamidine;

N-(3-Aminopropyl)-N'-(4-benzyloxyphenyl)-2-methylpiperidine-1-carboxamidine;

N-(3-Aminopropyl)-N'-(3-benzyloxyphenyl)-2-methylpiperidine-1-carboxamidine; and optical and geometrical isomers, oxide forms and tautomeric forms thereof, and also the pharmaceutically acceptable addition salts thereof.

26. A compound according to claim 1, wherein said compound is selected from:

N-(3-Aminopropyl)-2-methyl-N'-[4-(4-trifluoromethylbenzyloxy)phenyl]-piperidine-1-carboxamidine:

N-(3-Aminopropyl)-2-methyl-N'-(4-pentyloxyphenyl)piperidine-1-carboxamidine;

N-(3-Aminopropyl)-N'-[4-(2-methylbenzyloxy)phenyl]-N''-(3-methylbutyl)guanidine;

N-(3-Aminopropyl)-N'-(3-methylbutyl)-N''-[4-(4-trifluoromethylbenzyloxy)-phenyl]guanidine;

N-(3-Aminopropyl)-4-benzyl-N'-[4-(4-methylbenzyloxy)phenyl]piperidine-1-carboxamidine;

N-(3-Aminopropyl)-3-methyl-N'-[4-(4-methylbenzyloxy)phenyl]piperidine-1-carboxamidine;

N-(3-Aminopropyl)-4-methyl-N'-[4-(4-methylbenzyloxy)phenyl]piperidine-1-carboxamidine;

N-(3-Aminopropyl)-2-methyl-N'-[4-(4-methylbenzyloxy)phenyl]piperidine-1-carboxamidine, N-(3-Aminopropyl)-2-ethyl-N'-[4-(4-methylbenzyloxy)phenyl]piperidine-1-carboxamidine, N'-(3-Aminopropyl)-N-ethyl-N-isopropyl-N''-[4-(4-methylbenzyloxy)phenyl]-guanidine, N-(3-Aminopropyl)-4-benzyl-N'-[4-(2-methoxyethoxy)phenyl]piperidine-1-carboxamidine, N-(3-Aminopropyl)-2-methyl-N'-[4-(3-methylbut-2-enyloxy)phenyl]piperidine-1-carboxamidine, N'-(3-Aminopropyl)-N-ethyl-N-isopropyl-N''-[4-(3-methylbut-2-enyloxy)phenyl]-guanidine, N-(3-Aminopropyl)-4-benzyl-N'-[4-(3-methylbutoxy)phenyl]piperidine-1-carboxamidine, N-(3-Aminopropyl)-4-benzyl-N'-(4-decyloxyphenyl)piperidine-1-carboxamidine, N-(3-Aminopropyl)-N'-(4-decyloxyphenyl)-3-methylpiperidine-1-carboxamidine, N-(3-Aminopropyl)-N'-(4-decyloxyphenyl)-4-methylpiperidine-1-carboxamidine, N-(3-Aminopropyl)-N'-(4-decyloxyphenyl)-2-methylpiperidine-1-carboxamidine, N-(3-Aminopropyl)-N'-(4-decyloxyphenyl)-2-ethylpiperidine-1-carboxamidine, N'-(3-Aminopropyl)-N''-(4-decyloxyphenyl)-N-ethyl-N-isopropylguanidine, N-(3-Aminopropyl)-4-benzyl-N'-(4-propoxyphenyl)piperidine-1-carboxamidine, N-(3-Aminopropyl)-4-benzyl-N'-[4-(5-methylhexyloxy)phenyl]piperidine-1-carboxamidine, N-(3-Aminopropyl)-3-methyl-N'-[4-(5-methylhexyloxy)phenyl]piperidine-1-carboxamidine, N-(3-Aminopropyl)-4-methyl-N'-[4-(5-methylhexyloxy)phenyl]piperidine-1-carboxamidine, N-(3-Aminopropyl)-2-methyl-N'-[4-(5-methylhexyloxy)phenyl]piperidine-1-carboxamidine, N-(3-Aminopropyl)-2-ethyl-N'-[4-(5-methylhexyloxy)phenyl]piperidine-1-carboxamidine, N'-(3-Aminopropyl)-N-ethyl-N-isopropyl-N''-[4-(5-methylhexyloxy)phenyl]guanidine, N-(3-Aminopropyl)-N'-[4-(4-tert-butylbenzyloxy)phenyl]-3-methylpiperidine-1-carboxamidine, N-(3-Aminopropyl)-N'-[4-(4-tert-butylbenzyloxy)phenyl]-4-methylpiperidine-1- carboxamidine, N-(3-Aminopropyl)-4-benzyl-N'-[4-(4-cyanobenzyloxy)phenyl]piperidine-1-carboxamidine, N-(3-Aminopropyl)-N'-[4-(4-cyanobenzyloxy)phenyl]-3-methylpiperidine-1-carboxamidine, N-(3-Aminopropyl)-N'-[4-(4-cyanobenzyloxy)phenyl]-4-methylpiperidine-1-carboxamidine, N-(3-Aminopropyl)-N'-[4-(4-cyanobenzyloxy)phenyl]-2-methylpiperidine-1-carboxamidine, N-(3-Aminopropyl)-N'-[4-(4-cyanobenzyloxy)phenyl]-2-ethylpiperidine-1-carboxamidine, N'-(3-Aminopropyl)-N''-[4-(4-cyanobenzyloxy)phenyl]-N-ethyl-N-isopropyl-guanidine, N-(3-Aminopropyl)-4-benzyl-N'-[4-(2-cyanobenzyloxy)phenyl]piperidine-1-carboxamidine, N-(3-Aminopropyl)-N'-[4-(2-cyanobenzyloxy)phenyl]-3-methylpiperidine-1-carboxamidine, N-(3-Aminopropyl)-N'-[4-(2-cyanobenzyloxy)phenyl]-4-methylpiperidine-1-carboxamidine, N-(3-Aminopropyl)-N'-[4-(2-cyanobenzyloxy)phenyl]-2-methylpiperidine-1-carboxamidine, N-(3-Aminopropyl)-N'-[4-(2-cyanobenzyloxy)phenyl]-2-ethylpiperidine-1-carboxamidine, N-(3-Aminopropyl)-N'-[4-(2-cyclohexylethoxy)phenyl]-3-methylpiperidine-1-carboxamidine, N-(3-Aminopropyl)-N'-[4-(2-cyclohexylethoxy)phenyl]-4-methylpiperidine-1-carboxamidine, N-(3-Aminopropyl)-N'-[4-(2-cyclohexylethoxy)phenyl]-2-methylpiperidine-1-carboxamidine, N-(3-Aminopropyl)-N'-[4-(2-cyclohexylethoxy)phenyl]-2-ethylpiperidine-1-carboxamidine, N'-(3-Aminopropyl)-N''-[4-(2-cyclohexylethoxy)phenyl]-N-ethyl-N-isopropyl-guanidine, N-(3-Aminopropyl)-4-benzyl-N'-[4-(3-cyanopropoxy)phenyl]piperidine-1-carboxamidine,
N-(3-Aminopropyl)-N'-[4-(3-cyanopropoxy)phenyl]-3-methylpiperidine-1-carboxamidine,
N-(3-Aminopropyl)-N'-[4-(3-cyanopropoxy)phenyl]-4-methylpiperidine-1-carboxamidine,
N-(3-Aminopropyl)-N'-[4-(3-cyanopropoxy)phenyl]-2-methylpiperidine-1-carboxamidine,
N-(3-Aminopropyl)-N'-[4-(3-cyanopropoxy)phenyl]-2-ethylpiperidine-1-carboxamidine,
N'-(3-Aminopropyl)-N''-[4-(3-cyanopropoxy)phenyl]-N-ethyl-N-isopropyl-guanidine,
N-(3-Aminopropyl)-4-benzyl-N'-[4-(2-methylbenzyloxy)phenyl]piperidine-1-carboxamidine,
N-(3-Aminopropyl)-3-methyl-N'-[4-(2-methylbenzyloxy)phenyl]piperidine-1-carboxamidine,
N-(3-Aminopropyl)-4-methyl-N'-[4-(2-methylbenzyloxy)phenyl]piperidine-1-carboxamidine,
N-(3-Aminopropyl)-2-ethyl-N'-[4-(2-methylbenzyloxy)phenyl]piperidine-1-carboxamidine,
N'-(3-Aminopropyl)-N-ethyl-N-isopropyl-N''-[4-(2-methylbenzyloxy)phenyl]-guanidine,
N-(3-Aminopropyl)-4-benzyl-N'-[4-(3-trifluoromethoxybenzyloxy)phenyl]-piperidine-1-carboxamidine,
N-(3-Aminopropyl)-3-methyl-N'-[4-(3-trifluoromethoxybenzyloxy)phenyl]-piperidine-1-carboxamidine,
N-(3-Aminopropyl)-4-methyl-N'-[4-(3-trifluoromethoxybenzyloxy)phenyl]-piperidine-1-carboxamidine,
N-(3-Aminopropyl)-2-methyl-N'-[4-(3-trifluoromethoxybenzyloxy)phenyl]-piperidine-1-carboxamidine,
N-(3-Aminopropyl)-2-ethyl-N'-[4-(3-trifluoromethoxybenzyloxy)phenyl]-piperidine-1-carboxamidine,
N'-(3-Aminopropyl)-N-ethyl-N-isopropyl-N''-[4-(3-trifluoromethoxybenzyloxy)-phenyl]guanidine,
N-(3-Aminopropyl)-3-methyl-N'-[4-(4,4,4-trifluorobutoxy)phenyl]piperidine-1-carboxamidine,
N-(3-Aminopropyl)-4-methyl-N'-[4-(4,4,4-trifluorobutoxy)phenyl]piperidine-1-carboxamidine,
N-(3-Aminopropyl)-2-methyl-N'-[4-(4,4,4-trifluorobutoxy)phenyl]piperidine-1-carboxamidine,
N-(3-Aminopropyl)-2-ethyl-N'-[4-(4,4,4-trifluorobutoxy)phenyl]piperidine-1-carboxamidine,
N'-(3-Aminopropyl)-N-ethyl-N-isopropyl-N''-[4-(4,4,4-trifluorobutoxy)phenyl]-guanidine,
N-(3-Aminopropyl)-4-benzyl-N'-(4-pentyloxyphenyl)piperidine-1-carboxamidine,
N-(3-Aminopropyl)-3-methyl-N'-(4-pentyloxyphenyl)piperidine-1-carboxamidine,
N-(3-Aminopropyl)-4-methyl-N'-(4-pentyloxyphenyl)piperidine-1-carboxamidine,
N'-(3-Aminopropyl)-N-ethyl-N-isopropyl-N''-(4-pentyloxyphenyl)guanidine,
N-(3-Aminopropyl)-4-benzyl-N'-[4-(4-methanesulfonylbenzyloxy)phenyl]-piperidine-1-carboxamidine,
N-(3-Aminopropyl)-N'-[4-(4-methanesulfonylbenzyloxy)phenyl]-3-methylpiperidine-1-carboxamidine,
N-(3-Aminopropyl)-N'-[4-(4-methanesulfonylbenzyloxy)phenyl]-4-methylpiperidine-1-carboxamidine,
N-(3-Aminopropyl)-N'-[4-(4-methanesulfonylbenzyloxy)phenyl]-2-methylpiperidine-1-carboxamidine,
N-(3-Aminopropyl)-2-ethyl-N'-[4-(4-methanesulfonylbenzyloxy)phenyl]-piperidine-1-carboxamidine,
N'-(3-Aminopropyl)-N-ethyl-N-isopropyl-N''-[4-(4-methanesulfonylbenzyloxy)-phenyl]guanidine,
N-(3-Aminopropyl)-4-benzyl-N'-[4-(4-trifluoromethoxybenzyloxy)phenyl]-piperidine-1-carboxamidine,
N-(3-Aminopropyl)-3-methyl-N'-[4-(4-trifluoromethoxybenzyloxy)phenyl]-piperidine-1-carboxamidine,
N-(3-Aminopropyl)-4-methyl-N'-[4-(4-trifluoromethoxybenzyloxy)phenyl]-piperidine-1-carboxamidine,
N-(3-Aminopropyl)-2-methyl-N'-[4-(4-trifluoromethoxybenzyloxy)phenyl]-piperidine-1-carboxamidine,
N-(3-Aminopropyl)-2-ethyl-N'-[4-(4-trifluoromethoxybenzyloxy)phenyl]-piperidine-1-carboxamidine,
N'-(3-Aminopropyl)-N-ethyl-N-isopropyl-N''-[4-(4-trifluoromethoxybenzyloxy)-phenyl]guanidine,
N-(3-Amino-2,2-dimethylpropyl)-4-benzyl-N'-[4-(4-methylbenzyloxy)phenyl]-piperidine-1-carboxamidine,
N-(3-Amino-2,2-dimethylpropyl)-3-methyl-N'-[4-(4-methylbenzyloxy)phenyl]-piperidine-1-carboxamidine,
N-(3-Amino-2,2-dimethylpropyl)-4-methyl-N'-[4-(4-methylbenzyloxy)phenyl]-piperidine-1-carboxamidine,
N-(3-Amino-2,2-dimethylpropyl)-2-methyl-N'-[4-(4-methylbenzyloxy)phenyl]-piperidine-1-carboxamidine,
N-(3-Amino-2,2-dimethylpropyl)-2-ethyl-N'-[4-(4-methylbenzyloxy)phenyl]-piperidine-1-carboxamidine,
N'-(3-Amino-2,2-dimethylpropyl)-N-ethyl-N-isopropyl-N''-[4-(4-methylbenzyl-oxy)phenyl]guanidine,
N-(3-Amino-2,2-dimethylpropyl)-N'-[4-(2-methoxyethoxy)phenyl]-3-methylpiperidine-1-carboxamidine,
N-(3-Amino-2,2-dimethylpropyl)-N'-[4-(2-methoxyethoxy)phenyl]-4-methylpiperidine-1-carboxamidine,
N-(3-Amino-2,2-dimethylpropyl)-N'-[4-(2-methoxyethoxy)phenyl]-2-methyl-piperidine-1-carboxamidine,
N-(3-Amino-2,2-dimethylpropyl)-2-methyl-N'-[4-(3-methylbut-2-enyloxy)phenyl]-piperidine-1-carboxamidine,
N-(3-Amino-2,2-dimethylpropyl)-3-methyl-N'-[4-(3-methylbutoxy)phenyl]-piperidine-1-carboxamidine,
N-(3-Amino-2,2-dimethylpropyl)-4-methyl-N'-[4-(3-methylbutoxy)phenyl]-piperidine-1-carboxamidine,
N-(3-Amino-2,2-dimethylpropyl)-2-methyl-N'-[4-(3-methylbutoxy)phenyl]-piperidine-1-carboxamidine,
N-(3-Amino-2,2-dimethylpropyl)-2-ethyl-N'-[4-(3-methylbutoxy)phenyl]-piperidine-1-carboxamidine,
N'-(3-Amino-2,2-dimethylpropyl)-N-ethyl-N-isopropyl-N''-[4-(3-methylbutoxy)-phenyl]guanidine,
N-(3-Amino-2,2-dimethylpropyl)-N'-(4-decyloxyphenyl)-3-methylpiperidine-1-carboxamidine,
N-(3-Amino-2,2-dimethylpropyl)-N'-(4-decyloxyphenyl)-4-methylpiperidine-1-carboxamidine,
N-(3-Amino-2,2-dimethylpropyl)-N'-(4-decyloxyphenyl)-2-methylpiperidine-1-carboxamidine,
N-(3-Amino-2,2-dimethylpropyl)-N'-(4-decyloxyphenyl)-2-ethylpiperidine-1-carboxamidine,
N'-(3-Amino-2,2-dimethylpropyl)-N''-(4-decyloxyphenyl)-N-ethyl-N-isopropyl-guanidine,
N-(3-Amino-2,2-dimethylpropyl)-4-benzyl-N'-(4-propoxyphenyl)piperidine-1-carboxamidine,
N-(3-Amino-2,2-dimethylpropyl)-3-methyl-N'-(4-propoxyphenyl)piperidine-1-carboxamidine,
N-(3-Amino-2,2-dimethylpropyl)-4-methyl-N'-(4-propoxyphenyl)piperidine-1-carboxamidine,
N-(3-Amino-2,2-dimethylpropyl)-2-methyl-N'-(4-propoxyphenyl)piperidine-1-carboxamidine,
N-(3-Amino-2,2-dimethylpropyl)-2-ethyl-N'-(4-propoxyphenyl)piperidine-1-carboxamidine,
N'-(3-Amino-2,2-dimethylpropyl)-N-ethyl-N-isopropyl-N''-(4-propoxyphenyl)-guanidine,
N-(3-Amino-2,2-dimethylpropyl)-4-benzyl-N'-[4-(5-methylhexyloxy)phenyl]-piperidine-1-carboxamidine,
N-(3-Amino-2,2-dimethylpropyl)-3-methyl-N'-[4-(5-methylhexyloxy)phenyl]-piperidine-1-carboxamidine, N-(3-Amino-2,2-dimethylpropyl)-4-methyl-N'-[4-(5-methylhexyloxy)phenyl]-piperidine-1-carboxamidine,
N-(3-Amino-2,2-dimethylpropyl)-2-methyl-N'-[4-(5-methylhexyloxy)phenyl]-piperidine-1-carboxamidine,
N-(3-Amino-2,2-dimethylpropyl)-2-ethyl-N'-[4-(5-methylhexyloxy)phenyl]-piperidine-1-carboxamidine,
N'-(3-Amino-2,2-dimethylpropyl)-N-ethyl-N-isopropyl-N''-[4-(5-methylhexyl-oxy)phenyl]guanidine,
N-(3-Amino-2,2-dimethylpropyl)-N'-[4-(4-tert-butylbenzyloxy)phenyl]-3-methylpiperidine-1-carboxamidine,
N-(3-Amino-2,2-dimethylpropyl)-N'-[4-(4-tert-butylbenzyloxy)phenyl]-4-methylpiperidine-1-carboxamidine,
N-(3-Amino-2,2-dimethylpropyl)-N'-[4-(4-tert-butylbenzyloxy)phenyl]-2-methylpiperidine-1-carboxamidine,
N-(3-Amino-2,2-dimethylpropyl)-N'-[4-(4-tert-butylbenzyloxy)phenyl]-2-ethyl-piperidine-1-carboxamidine,
N'-(3-Amino-2,2-dimethylpropyl)-N''-[4-(4-tert-butylbenzyloxy)phenyl]-N-ethyl-N-isopropylguanidine,
N-(3-Amino-2,2-dimethylpropyl)-4-benzyl-N'-[4-(4-cyanobenzyloxy)phenyl]-piperidine-1-carboxamidine,
N-(3-Amino-2,2-dimethylpropyl)-N'-[4-(4-cyanobenzyloxy)phenyl]-3-methyl-piperidine-1-carboxamidine,
N-(3-Amino-2,2-dimethylpropyl)-N'-[4-(4-cyanobenzyloxy)phenyl]-4-methyl-piperidine-1-carboxamidine,
N-(3-Amino-2,2-dimethylpropyl)-N'-[4-(4-cyanobenzyloxy)phenyl]-2-methyl-piperidine-1-carboxamidine,
N'-(3-Amino-2,2-dimethylpropyl)-N''-[4-(4-cyanobenzyloxy)phenyl]-N-ethyl-N-isopropylguanidine,
N-(3-Amino-2,2-dimethylpropyl)-N'-[4-(2-cyanobenzyloxy)phenyl]-3-methyl-piperidine-1-carboxamidine,
N-(3-Amino-2,2-dimethylpropyl)-N'-[4-(2-cyanobenzyloxy)phenyl]-2-methyl-piperidine-1-carboxamidine,
N'-(3-Amino-2,2-dimethylpropyl)-N''-[4-(2-cyanobenzyloxy)phenyl]-N-ethyl-N-isopropylguanidine,
N-(3-Amino-2,2-dimethylpropyl)-4-benzyl-N'-[4-(2-cyclohexylethoxy)phenyl]-piperidine-1-carboxamidine,
N-(3-Amino-2,2-dimethylpropyl)-N'-[4-(2-cyclohexylethoxy)phenyl]-3-methyl-piperidine-1-carboxamidine,
N-(3-Amino-2,2-dimethylpropyl)-N'-[4-(2-cyclohexylethoxy)phenyl]-4-methyl-piperidine-1-carboxamidine,
N-(3-Amino-2,2-dimethylpropyl)-N'-[4-(2-cyclohexylethoxy)phenyl]-2-methyl-piperidine-1-carboxamidine,
N-(3-Amino-2,2-dimethylpropyl)-N'-[4-(2-cyclohexylethoxy)phenyl]-2-ethyl-piperidine-1-carboxamidine,
N'-(3-Amino-2,2-dimethylpropyl)-N''-[4-(2-cyclohexylethoxy)phenyl]-N-ethyl-N-isopropylguanidine,
N-(3-Amino-2,2-dimethylpropyl)-4-benzyl-N'-[4-(3-cyanopropoxy)phenyl]-piperidine-1-carboxamidine,
N-(3-Amino-2,2-dimethylpropyl)-N'-[4-(3-cyanopropoxy)phenyl]-3-methylpiperidine-1-carboxamidine,
N-(3-Amino-2,2-dimethylpropyl)-N'-[4-(3-cyanopropoxy)phenyl]-4-methylpiperidine-1-carboxamidine,
N-(3-Amino-2,2-dimethylpropyl)-N'-[4-(3-cyanopropoxy)phenyl]-2-ethylpiperidine-1-carboxamidine,
N-(3-Amino-2,2-dimethylpropyl)-4-benzyl-N'-[4-(2-methylbenzyloxy)phenyl]-piperidine-1-carboxamidine,
N-(3-Amino-2,2-dimethylpropyl)-3-methyl-N'-[4-(2-methylbenzyloxy)phenyl]-piperidine-1-carboxamidine,
N-(3-Amino-2,2-dimethylpropyl)-2-methyl-N'-[4-(2-methylbenzyloxy)phenyl]-piperidine-1-carboxamidine,
N-(3-Amino-2,2-dimethylpropyl)-2-ethyl-N'-[4-(2-methylbenzyloxy)phenyl]-piperidine-1-carboxamidine,
N-(3-Amino-2,2-dimethylpropyl)-4-benzyl-N'-[4-(3-trifluoromethoxybenzyloxy)-phenyl]piperidine-1-carboxamidine,
N-(3-Amino-2,2-dimethylpropyl)-3-methyl-N'-[4-(3-trifluoromethoxybenzyloxy)-phenyl]piperidine-1-carboxamidine,
N-(3-Amino-2,2-dimethylpropyl)-2-methyl-N'-[4-(3-trifluoromethoxybenzyl-oxy)phenyl]piperidine-1-carboxamidine,
N-(3-Amino-2,2-dimethylpropyl)-2-ethyl-N'-[4-(3-trifluoromethoxybenzyloxy)-phenyl]piperidine-1-carboxamidine,
N-(3-Amino-2,2-dimethylpropyl)-4-benzyl-N'-[4-(4,4,4-trifluorobutoxy)phenyl]-piperidine-1-carboxamidine,
N-(3-Amino-2,2-dimethylpropyl)-4-methyl-N'-[4-(4,4,4-trifluorobutoxy)phenyl]-piperidine-1-carboxamidine,
N-(3-Amino-2,2-dimethylpropyl)-2-ethyl-N'-[4-(4,4,4-trifluorobutoxy)phenyl]-piperidine-1-carboxamidine,
N-(3-Amino-2,2-dimethylpropyl)-4-benzyl-N'-(4-pentyloxyphenyl)piperidine-1-carboxamidine,
N-(3-Amino-2,2-dimethylpropyl)-2-methyl-N'-(4-pentyloxyphenyl)piperidine-1-carboxamidine,
N-(3-Amino-2,2-dimethylpropyl)-2-ethyl-N'-(4-pentyloxyphenyl)piperidine-1-carboxamidine,
N-(3-Amino-2,2-dimethylpropyl)-4-benzyl-N'-[4-(4-methanesulfonylbenzyloxy)-phenyl]piperidine-1-carboxamidine,
N-(3-Amino-2,2-dimethylpropyl)-N'-[4-(4-methanesulfonylbenzyloxy)phenyl]-3-methylpiperidine-1-carboxamidine,
N-(3-Amino-2,2-dimethylpropyl)-N'-[4-(4-methanesulfonylbenzyloxy)phenyl]-4-methylpiperidine-1-carboxamidine,
N-(3-Amino-2,2-dimethylpropyl)-N'-[4-(4-methanesulfonylbenzyloxy)phenyl]-2-methylpiperidine-1-carboxamidine,
N-(3-Amino-2,2-dimethylpropyl)-2-ethyl-N'-[4-(4-methanesulfonylbenzyloxy)-phenyl]piperidine-1-carboxamidine,
N'-(3-Amino-2,2-dimethylpropyl)-N-ethyl-N-isopropyl-N''-[4-(4-methanesul-fonylbenzyloxy)phenyl]guanidine,
N-(3-Amino-2,2-dimethylpropyl)-4-benzyl-N'-[4-(4-trifluoromethoxybenzyloxy)-phenyl]piperidine-1-carboxamidine,
N-(3-Amino-2,2-dimethylpropyl)-4-methyl-N'-[4-(4-trifluoromethoxybenzyloxy)-phenyl]piperidine-1-carboxamidine,
N-(3-Amino-2,2-dimethylpropyl)-2-methyl-N'-[4-(4-trifluoromethoxybenzyloxy)-phenyl]piperidine-1-carboxamidine,
N-(3-Amino-2,2-dimethylpropyl)-2-ethyl-N'-[4-(4-trifluoromethoxybenzyloxy)-phenyl]piperidine-1-carboxamidine,
N'-(3-Amino-2,2-dimethylpropyl)-N-ethyl-N-isopropyl-N''-[4-(4-trifluoro-methoxybenzyloxy)phenyl]guanidine, and
optical and geometrical isomers, oxide forms and tautomeric forms thereof, and also the pharmaceutically acceptable addition salts thereof.

* * * * *